United States Patent
Becker

(10) Patent No.: US 7,846,124 B2
(45) Date of Patent: Dec. 7, 2010

(54) PUNCTAL ANCHOR FOR LACRIMAL STENT, INTRODUCER TOOL AND METHOD

(76) Inventor: Bruce B. Becker, 5363 Balboa Blvd., Suite 246, Encino, CA (US) 91316

(*) Notice: Subject to any disclaimer, the term of this patent is extended or adjusted under 35 U.S.C. 154(b) by 10 days.

(21) Appl. No.: 12/116,875

(22) Filed: May 7, 2008

(65) Prior Publication Data

US 2009/0281621 A1    Nov. 12, 2009

(51) Int. Cl.
*A61M 5/00* (2006.01)
(52) U.S. Cl. .................................................. 604/8
(58) Field of Classification Search ............ 604/8, 604/11, 12, 27, 28, 93.01, 94.01, 164.01, 604/264
See application file for complete search history.

(56) References Cited

U.S. PATENT DOCUMENTS

| | | | | |
|---|---|---|---|---|
| 1,906,678 | A | * | 5/1933 | Wappler .............. 604/170.01 |
| 4,305,395 | A | | 12/1981 | Martinez |
| 4,380,239 | A | | 4/1983 | Crawford et al. |
| 4,756,708 | A | * | 7/1988 | Martin ................ 604/170.03 |
| 5,169,386 | A | * | 12/1992 | Becker et al. ............. 606/192 |
| 5,318,513 | A | * | 6/1994 | Leib et al. .................... 604/8 |
| 5,997,562 | A | | 12/1999 | Zadno-Azizi et al. |
| 6,083,188 | A | | 7/2000 | Becker |
| 6,113,567 | A | * | 9/2000 | Becker ........................ 604/8 |
| 6,238,364 | B1 | * | 5/2001 | Becker ........................ 604/8 |
| 6,383,192 | B1 | | 5/2002 | Kurihashi |
| 6,605,108 | B2 | | 8/2003 | Mendius et al. |
| 7,559,925 | B2 | * | 7/2009 | Goldfarb et al. ........... 604/510 |
| 2006/0020248 | A1 | * | 1/2006 | Prescott .................... 604/294 |
| 2007/0299462 | A1 | | 12/2007 | Becker |

FOREIGN PATENT DOCUMENTS

WO    2007139919    12/2007

* cited by examiner

*Primary Examiner*—Tatyana Zalukaeva
*Assistant Examiner*—Benedict L Hanrahan
(74) *Attorney, Agent, or Firm*—Charmasson, Buchaca & Leach, LLP

(57) ABSTRACT

A device and method for performing stenting and intubation of the nasolacrimal system to treat for stenosis or obstruction includes a semi-rigid tubular guide sleeve through which a flexible tubular stent, having an oversized length, is inserted from a punctal opening into the nasal cavity. The guide sleeve is removed and a resilient, radially expandable punctal anchor is placed through the punctal opening, to contact the stent and hold it in place. An introducer device having a hollow tubular core and a coaxially mounted, axially translatable outer sheath is provided to facilitate placement of the anchor. The anchor is stretched over the distal end of the core and the stent threaded into the central lumen of the core. Once the anchor is in place, the sheath is translated to push the anchor off the distal end. Excess stent at its proximal end is then trimmed off.

36 Claims, 16 Drawing Sheets

PUNCTAL ANCHOR FOR LACRIMAL STENT, INTRODUCER TOOL AND METHOD

FIELD OF THE INVENTION

The present invention relates to devices used for normalizing the flow of fluid in tubular organs of human bodies that have been injured by a disease or an accident. More specifically, the invention relates to treating punctal, canalicular and nasolacrimal duct damage, stenosis or obstruction.

BACKGROUND

The orbital portion of the lacrimal gland is located in the superotemporal orbit and the palpebral portion of the lacrimal gland is located on the posterior surface of the superotemporal upper lid. The lacrimal gland produces the aqueous portion of the tear film. Ductules from the orbital portion of the lacrimal gland pass through the adjacent palpebral lacrimal gland to empty in the superior conjunctival cul-de-sac. Smaller accessory lacrimal glands in the upper and lower lids also contribute to tear production. The tears bathe the surface of the eye and then drain into the nose via the lacrimal drainage system.

Referring now to FIGS. 1 and 2, the lacrimal drainage system comprises a pair of small openings, namely the superior punctum 2 and inferior punctum 3, are located on the medial upper and lower lids of the eye 1. Tears flow into these puncta which lead to two small diameter delicate tubes, namely, the superior canaliculus 4 and the inferior canaliculus 5. The canaliculi join together as a short common canaliculus 6 that enters into the larger lacrimal sac 7. The tears then flow from the lacrimal sac down the nasolacrimal duct 8 and out an opening 9 which empties into the nose on the lateral nasal wall 10 and on to the nasal floor 11 beneath the inferior turbinate 12. This space beneath the inferior turbinate is called the inferior meatus 13 of the nasal cavity.

The canaliculi can become obstructed or stenotic on a congenital basis, or acquired as a result of some trauma such as lacerations, inflammation, side effects of chemotherapy, such as taxotere or five-fluorouracil—which may also affect the nasolacrimal duct—or the obstruction can be idiopathic. Once obstructed, tears can no longer drain from the surface of the eye through the lacrimal drainage system into the nose. As a result tears well up in the eye, and run down the face. Excess tears blur the vision and the patient has to constantly dab the eye.

The nasolacrimal duct can be obstructed on a congenital basis, occurring in about 2% to 6% of newborns, or acquired as a result of some trauma, sarcoidosis or other diseases, but most commonly is idiopathic. When the nasolacrimal duct is obstructed, tears stagnate in the lacrimal sac where bacteria multiply leading to infection. The result is a painful enlargement of the lacrimal sac swollen with pus, and a discharge over the eye.

A congenital nasolacrimal duct obstruction often resolves spontaneously, or with the use of antibiotic drops and massage of the lacrimal sac. However, a significant number of patients require surgical treatment.

Canalicular obstruction or stenosis, and nasolacrimal duct obstructions are often treated by forming a passageway through the obstruction or stenoic tissue using a surgical probe which is a small diameter, blunt-ended rod made of solid steel, bronze, silver or other metal. A flattened area in the center of the probe facilitates its manipulation.

The passageway through the nasolacrimal duct can be further dilated using a balloon catheter through dacryocystoplasty (DCP). Often the treatment of nasolacrimal duct obstruction in adults involves the creation of a new passage from the lacrimal sac directly into the nasal cavity bypassing the nasolacrimal duct according to a procedure called dacryocystorhinostomy (DCR). Both procedures are disclosed in my U.S. Pat. No. 5,169,386 incorporated herein by this reference.

Intubation of the lacrimal system is often performed after lacrimal surgery or as a primary treatment for nasolacrimal duct obstruction, canalicular stenosis, or canalicular laceration, in order to keep the lacrimal passageway open and prevent scars from permanently clogging the canaliculi or nasolacrimal duct. In cases of canalicular or nasolacrimal duct obstruction from chemotherapy, intubation is performed as quickly as possible to prevent complete, irreversible closure. Intubation typically involves placement of a flexible silicone tube looped through both canaliculi where both ends extend down the nasolacrimal duct and into the nose. Such intubation is described in Martinez, U.S. Pat. No. 4,305,395, and Crawford et al., U.S. Pat. No. 4,380,239, both of which are incorporated herein by this reference.

A number of types of intubation devices are available. The most common type is a silicone tube having a metal probe attached on each end as in Crawford et al cited above. A probe on one end is pushed through one of the punctum, its canaliculus, the lacrimal sac, and down the nasolacrimal duct into the nose. The probe is grasped in the nose by the surgeon and pulled out the naris. The tube follows the probe. The probe on the other end of the tube is pushed through the second punctum, its canaliculus, the lacrimal sac, and down the nasolacrimal duct into the nose, grasped by the surgeon, and pulled out the naris bringing the other end of the tube with it. The probes are removed and the two ends of the tube are tied together and left hanging in the nose. The tube is removed several months later by pulling it up the lacrimal system, cutting it, and removing it through one of the puncta.

The above process presents several difficulties. First, the nasal opening to the nasolacrimal duct is extremely difficult to visualize during surgery or examination, and very difficult to access with an instrument, making the grasping of the probe difficult. Rigid and flexible endoscopes usually cannot fit between the inferior turbinate and the lateral nasal wall. Direct visualization using a nasal speculum and a headlight is usually not possible. Placing an instrument near the nasolacrimal duct opening through the nose can be very difficult. A probe or tube sticking out of the nasolacrimal duct opening in the nose will often be buried in the surrounding soft tissue of the nasal floor or lateral wall. Further, there is often edema of the inferior turbinate and nasal mucosa, and sometimes bleeding which make it more difficult to locate, access, grasp, and retrieve the probe, tube, suture or other item coming out of the nasolacrimal duct opening. It is often difficult if not impossible to position a suction catheter in the inferior meatus in order to remove blood around the nasolacrimal duct opening.

One way of trying to confirm without visualization whether the probe, tube or other item has penetrated into the nose is by touch. The surgeon will typically introduce a metal instrument through the external naris into the nose and try blindly to touch the tip of the item sticking out of the nasolacrimal duct opening until a contact between the two is felt. Detecting contact takes quite a bit of skill and experience. Often, if no contact is felt, the surgeon may remove the item and reinsert it, then try again to confirm penetration. These repeated procedures can cause multiple traumas to the lacrimal drainage system.

Another commonly used intubation device is the MINI-MONOKA device available from FCI Ophthalmics Inc. of Marshfield Hills, Mass. This device consists of a short silicone tube which is generally not long enough to extend into the nasolacrimal duct. The proximal end of the tube is formed into a punctal plug to anchor it in a punctum. The tube is threaded through a punctum and canaliculus into the lacrimal sac, and can be used to stent the canaliculus but typically not the nasolacrimal duct.

Another type of intubation device is the MONO-CRAWFORD device available from FCI Ophthalmics Inc. of Marshfield Hills, Mass. which is similar to the MINI-MONOKA device but provides a longer flexible stent. It also has a puntal plug at its proximal end. The distal end must be threaded through the lacrimal system from the eye side but is too flexible to be pushed on its own through the system.

The RITLENG probe available from FCI Ophthalmics Inc. of Marshfield Hills, Mass. has been designed to help this problem. It is a hollow metal tube with a slit-like opening along its entire length which is placed through the punctum, canaliculus, lacrimal sac, and down the nasolacrimal duct into the nose. A separate polyethylene tube that is attached to a flexible silicone tube having a punctal plug formed on its proximal end is threaded through the hollow probe into the nose. The polyethylene tube is located and grasped in the nose by the surgeon and pulled out the naris. The hollow probe is then withdrawn out the punctum. The silicone tube passes through the slit so that the probe can be removed. The plug on the proximal end of the silicone tube is then seated in the punctum. The distal end of the tube is then cut just inside the external naris. Therefore, the RITLENG tube must still be retrieved and pulled out the nose. This can be difficult or impossible in some cases as detailed above.

Both the MINI-MONOKA and RITLENG devices use punctum plugs integrally formed onto the proximal ends of flexible tubes. Therefore, the length of the tube can only be altered during surgery by cutting the distal end. The RITLENG and MONO-CRAWFORD tubes must be retrieved in the nose and brought out the nose to achieve this. The MINI-MONOKA tube is too short to have its length altered in vivo.

My U.S. patent application Publication No. 2007/0276314 incorporated herein by this reference describes a silicone tube with a balloon on the end. It extends from the punctum and canaliculus into the lacrimal sac. A balloon on the end of the tube in the lacrimal sac is then inflated to keep the tube in position. The tube does not extend into the nasolacrimal duct.

The FCI company has a plug that is placed in the punctum in order to obstruct the punctum and prevent tear drainage through the lacrimal system into the nose. This is used for patients with dry eye syndrome to keep more tears in the tear film over the eye. The FCI plug has a lumen with a proximal opening and a distal closed end. A metal probe at the end of an inserter expands the tube along its longitudinal axis to reduce the diameter during insertion. When the plug is in place then the inserter is withdrawn and the plug contracts along its longitudinal axis and thus increases radially so that it will be tight in the punctum and not fall out. The lumen does not expand. The plug cannot be placed on a separate silicone tube. The device is not expanded radially by the inserter, but rather is expanded longitudinally which decreases its outside and inside diameter.

I show in International Publication No. WO 2007/139919 a lacrimal stent that uses a soft tube, ideally silicone, that has a higher durometer reinforcer tube within the closed distal end. The silicone stent can be placed in the lacrimal system through the punctum, canaliculus, common canaliculus, lacrimal sac, and nasolacrimal duct into the nose. The silicone tube and reinforcer have holes in the sidewalls in the distal end. A hollow irrigating probe with holes in the sidewalls is used to push the silicone tube into the lacrimal system and the distal end into the nose. The irrigating probe allows fluorescein stained fluid to be irrigated through the tube and recovered in the nose to confirm that the silicone tube has penetrated all obstructions and reached the nasal cavity. The reinforcer resists the probe puncturing the distal end of the silicone tube. The silicone tube does not need to be retrieved in the nose.

There are however, certain problems that have been encountered. If there is a very tight nasolacrimal duct or canaliculus, then the probe may still puncture through the end of the silicone tube and reinforcer or otherwise rupture the tube. In this event it is impossible to emplace the silicone tube in the lacrimal system.

Another problem is that the distance from the punctum through the lacrimal system to the nasal floor is quite variable between and within age groups. Furthermore, the angle at which the silicone tube and enclosed probe exit the nasolacrimal duct in the nose is different among patients. The angle of exit determines where the probe and tube hit the nasal floor. That is because the nasal floor is concave upward where it comes off the lateral nasal wall. The point at which the probe and tube hit the nasal floor is a factor in determining the length of silicone tube needed. Silicone tubes of many different lengths must be available for the surgeons's use for these reasons.

The instant invention results from attempts to avoid the aforesaid problems and provide more efficient, simpler and safer procedures in the treatment of nasolacrimal duct obstructions, including improved probe use and function, and providing improved irrigation, dilatation, and/or intubation.

SUMMARY

The instant embodiments provide devices and method to better treat obstructions in the nasolacrimal system.

In some embodiments there is provided a method for stenting a patient's nasolacrimal duct which comprises the steps of: selecting an elongated tubular guide sleeve and an elongated flexible stent; wherein said guide sleeve has an open proximal end and an open distal end, and defines an internal channel; and, wherein said stent has a proximal extremity and a distal extremity; and, wherein said stent is located within said channel; pushing said sleeve carrying said stent through a patient's punctum, canaliculus, lacrimal sac, nasolacrimal duct and into the nasal cavity; confirming that the distal end of said sleeve is located in said nasal cavity; proximally withdrawing said guide sleeve while leaving said stent in place; and, affixing a punctal anchor to said stent.

In some embodiments the method further comprises: removing an excess section of said stent located proximally from said anchor after said affixing. In some embodiments said removing comprises cutting the stent so that its proximal extremity is flush with the anchor. In some embodiments the method further comprises: stiffening said sleeve prior to said pushing. In some embodiments said stiffening comprises: selecting said stent to be tubular defining a central lumen; and, engaging said lumen with an oblong rod having a first flexural rigidity which is more rigid than a second flexural rigidity of said stent. In some embodiments said selecting an elongated flexible stent further comprises: choosing said stent to be tubular; and, wherein said distal extremity is closed and said proximal extremity is open.

In some embodiments said affixing comprises: choosing said stent to have a proximal portion of a given cross-sectional dimension; selecting said anchor to have a resiliently expandable bore having a resting diameter smaller than said dimension; expanding said bore; inserting said proximal portion of said stent into said bore after said expanding; and, collapsing said bore onto said stent.

In some embodiments said affixing comprises: selecting said anchor to have a resiliently reducable diameter; reducing the diameter of said anchor; inserting said anchor while in a reduced diameter state into an opening in said proximal extremity of said stent; and, allowing said anchor to resiliently return to a non-reduced diameter state, thereby forming a friction fit with said stent.

In some embodiments said method is practiced in absence of retrieving a portion of said stent out the naris. In some embodiments said method is practiced in absence of visualizing said stent within said nasal cavity.

In some embodiments said confirming comprises: injecting a tracing fluid through the guide sleeve; and recovering traces of said fluid in said nasal cavity.

In some embodiments the method further comprises: inserting a hollow stiffening rod having a distal hole, into the channel of said sleeve; and, wherein said injecting comprises: attaching a source for said fluid to a proximal connector on said rod.

In some embodiments said selecting of said guide sleeve comprises: choosing said guide to have at least one radial hole near said distal end of said guide sleeve.

In some embodiments said sleeve has an axial length and wherein said rod has a maximum length dimension greater than two times said axial length.

In some embodiments the method further comprises injecting a lubricant through said channel during said step of pushing. In some embodiments the method further comprises; connecting a suction device to the proximal end of said sleeve; and, suctioning debris out of said system through said channel. In some embodiments the method further comprises injecting medication into said system through said channel.

In some embodiments there is provided a method for stenting a patient's nasolacrimal duct which comprises the steps of: selecting an elongated tubular guide sleeve defining an internal channel and having an open proximal end and an open distal end; inserting said sleeve through a patient's punctum, canaliculus, lacrimal sac, nasolacrimal duct and into the nasal cavity; confirming that the distal end of said sleeve is located in said nasal cavity; selecting an elongated flexible stent having a proximal extremity and a distal extremity; pushing said stent into the proximal end of said guide sleeve until said distal extremity is located in the nasal cavity; proximally withdrawing said guide sleeve while leaving said stent in place; and, affixing a punctal anchor to said stent.

In some embodiments said affixing comprises: placing said anchor in said punctum adjacent to a portion of said stent; and, removing an excess section of said stent located proximally from said portion.

In some embodiments the method further comprises rigidizing said stent prior to said pushing, wherein said rigidizing comprises: selecting said stent to be tubular defining a central lumen; and, engaging said lumen with an oblong rod having a first flexural rigidity which is more rigid than a second flexural rigidity of said stent.

In some embodiments the method further comprises rigidizing said guide sleeve prior to said inserting, wherein said rigidizing comprises engaging said guide sleeve with an oblong probe having a flexural rigidity greater than that of said guide.

In some embodiments selecting said guide comprises choosing said guide to have an unobstructed central channel having sufficient rigidity and continuity to allow pushing said stent all the way through said guide from force applied to said stent on portions extending from said proximal end of said guide.

In some embodiments there is provided a method for stenting a passageway formed by dacryocystorhinostomy ("DCR") which comprises the steps of: selecting an elongated tubular guide sleeve and an elongated flexible stent; wherein said guide sleeve has an open proximal end and an open distal end, and defines an internal channel; and, wherein said stent has a proximal extremity and a distal extremity; and, wherein said stent is located within said channel; pushing said sleeve carrying said stent through said passageway and into the nasal cavity; confirming that the distal end of said sleeve is located in said nasal cavity; proximally withdrawing said guide sleeve while leaving said stent in place; and, affixing a punctal anchor to said stent.

In some embodiments there is provided a multi-functional surgical tool for the treatment of nasolacrimal obstruction, stenosis or damage which comprises: a first elongated tubular guide sleeve having proximal and distal ends, and defining an internal channel; said sleeve being sized and having a first flexural rigidity to be introduced into a patient's nasolacrimal duct through one of said patient's canaliculi by pushing on portions of said sleeve located proximal to said one of said patient's canaliculi; an elongated tubular stent having proximal and distal extremities, and defining an internal lumen; a first stiffening rod diametrically sized to engage said lumen; said stent having a second flexural rigidity; wherein said second rigidity is less rigid than said first rigidity; and, said stent being sized and cross-sectionally shaped to engage said channel while said stent is being engaged by said rod; and, an anchor sized to intimately and oversizedly engage said punctum.

In some embodiments said first sleeve, said stent and said rod are coaxial. In some embodiments said sleeve has a first length; said stent has a second length greater than said first length; and, said stiffening rod has a length at least equal to said second length. In some embodiments said first length is between about 1 and 15 inches. In some embodiments said sleeve has a maximum cross-sectional dimension of between about 0.014 inch and 0.060 inch. In some embodiments said internal channel has a substantially smooth continuous surface. In some embodiments said guide has at least one radial hole through a sidewall near said distal end.

In some embodiments the tool further comprises a first connector at a proximal end of said rod adapted to releasably connect to a pressurized fluid source. In some embodiments the tool further comprises an irrigation device connected to said first connector. In some embodiments the tool further comprises a suction device connected to said first connector.

In some embodiments the tool further comprises an introducer for affixing said anchor to said stent. In some embodiments the introducer comprises: an outer tubular sheath; a tubular inner body having a distal end portion sized to stretchingly engage an axial bore through said anchor, and said body being shaped to have an inner cavity sized to accommodate a portion of said stent therein; and, said body slidingly engaging said sheath. In some embodiments the introducer further comprises a flaring spike having a rounded distal end section of a first diameter and a proximal section having a second diameter larger than said first diameter; and, wherein said proximal section is releasably attachable to said distal end portion of said body. In some embodiments the introducer further comprises means for axially sliding said body with respect to said sheath.

DESCRIPTION OF THE EXEMPLARY EMBODIMENTS

Initial probing of the lacrimal drainage system can be performed with the irrigating cannula in order to form or confirm the existence of a passageway through the system to the nose.

Figure 1:
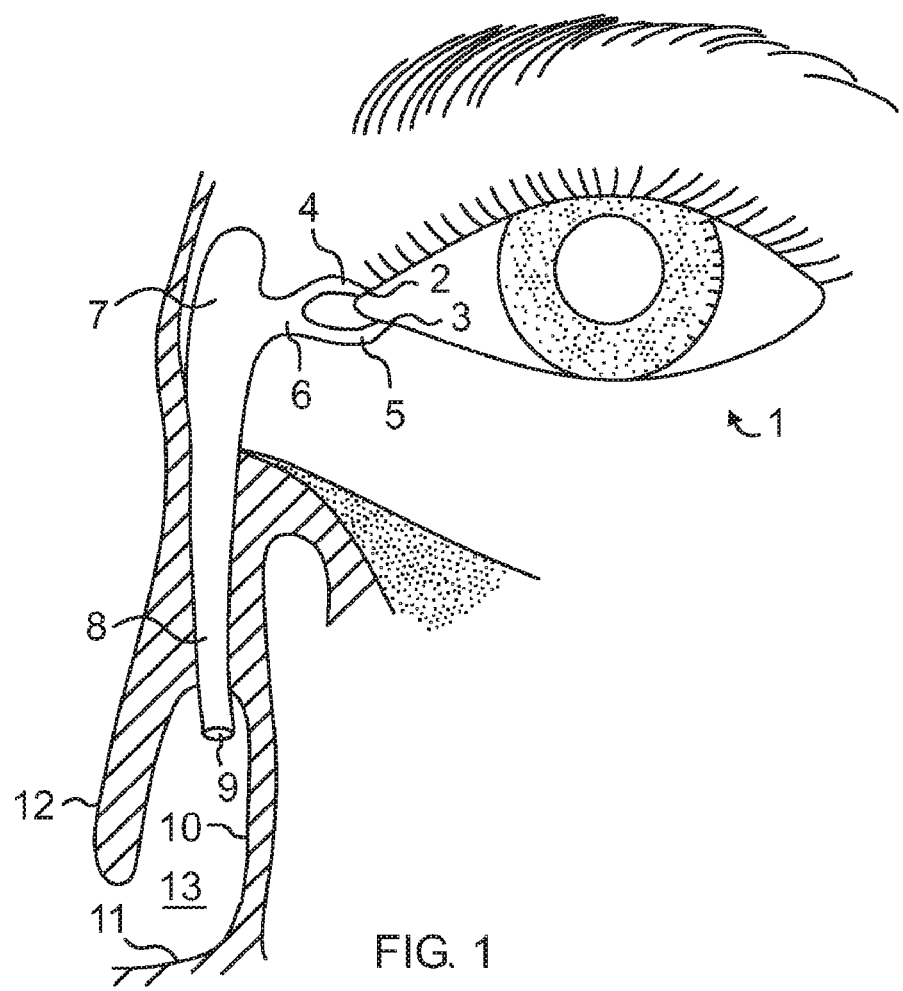
FIG. 1 is a cross-sectional frontal illustration of the lacrimal drainage system of a human patient.
Figure 2:
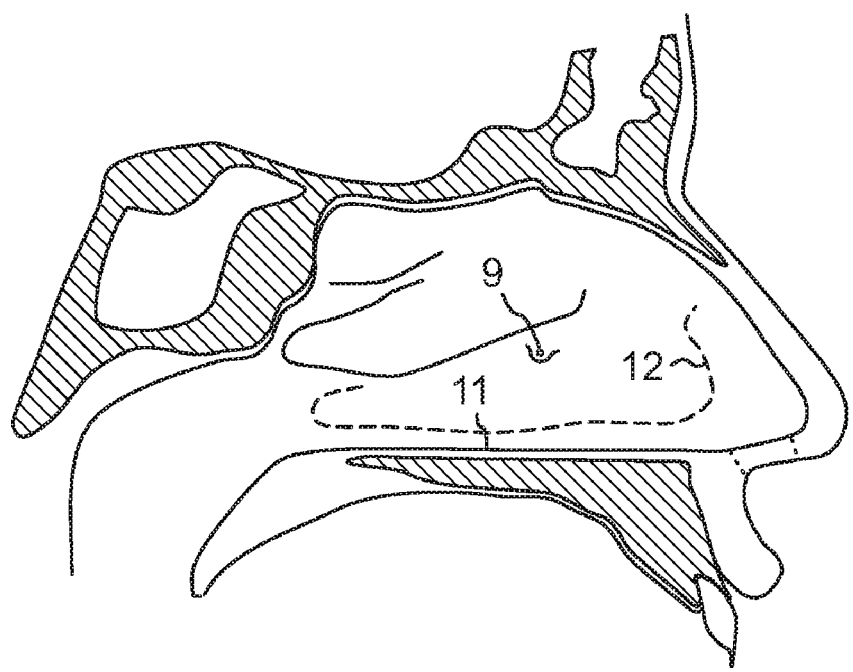
FIG. 2 is a partial, cross-sectional side illustration of the system of FIG. 1.
Figure 3:
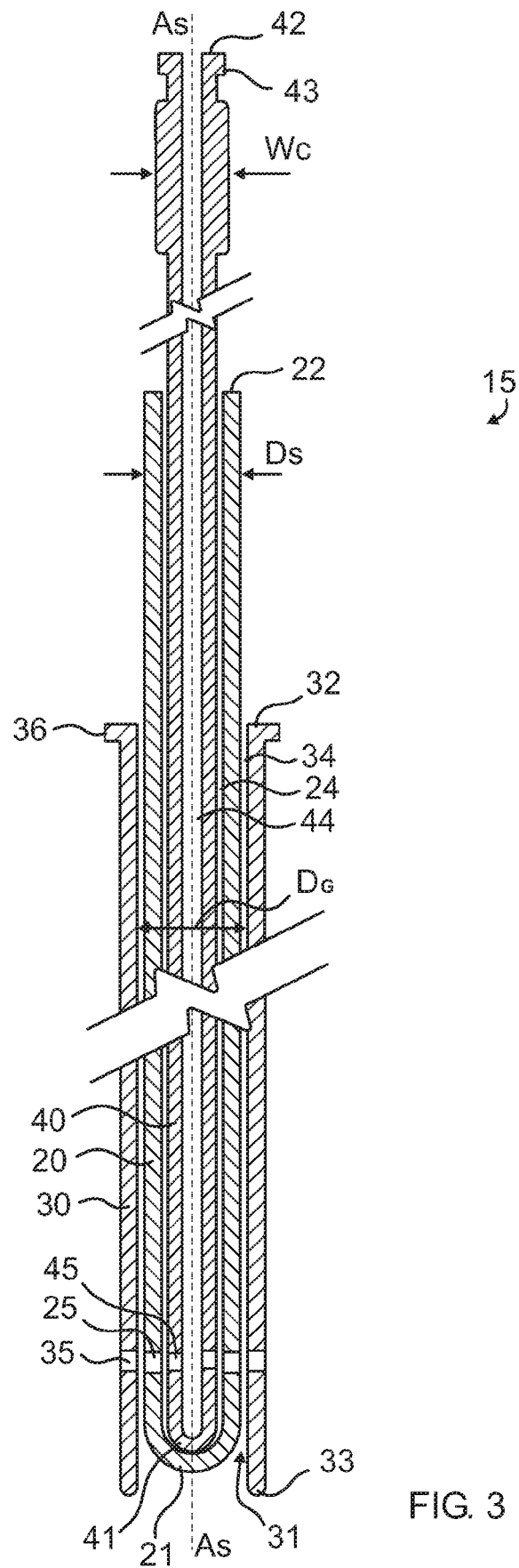
FIG. 3 illustrates the applicator sleeve engaged by a flexible stent and rigidizing rod.

Referring now to the drawing, there is shown in FIG. 3 a the cross-sectional view of a stent insertion structure 15 for inserting a flexible stent into a patient's lacrimal drainage system from one of the puncta into the nasal cavity. This structure combines an elongated, hollow, flexible stent 20 coaxially mounted over a semi-rigid, hollow rigidizing rod 40. The stent and rod are coaxially engaged in the axial channel 34 of a protective, elongated, tubular applicator sleeve 30. The size of the combined structure is selected by the surgeon to allow it to be inserted into the lacrimal drainage system.

The components of the combined insertion structure 15, namely the sleeve, stent and rod, are shaped cylindrically so that they nest intimately together in order to minimize the diametric radial cross-sectional diameter of the structure and thereby minimize the invasiveness of the structure. The combined structure is further selected so that the structure has the proper range of rigidity, column strength and resistance to lateral bending that allow it to be used in the procedure described below. In general, it has a slight degree of flexibility resulting from the choice of material and its dimensions to allow it to navigate the bends and angles of the lacrimal system but also has sufficient rigidity to be pushed through the lacrimal system and any encountered stenoses or obstructions into the nasal cavity. This arrangement also allows the sleeve to bear the insertion forces placed on the combined structure thereby avoiding penetration of the rod through the closed distal extremity of the stent. The preferred flexural rigidity of the entire combined structure will depend on the anatomy of the patient and is selected to provide the above functionality while allowing the surgeon to manipulate the combined structure from the proximal side only. In other words, the surgeon can emplace the combined structure in absence of any guidewire, and while manipulating only those parts of the structure that remain exposed proximally from the punctum. The physical characteristics of the individual components can be selected to accommodate the above defined flexural rigidity requirements.

The stent 20 is formed from a length of flexible tubing made from a biocompatible material such as silicone, polyethylene, or other material known to those skilled in the art. The tubular stent is hollow having a closed, rounded distal extremity 21 and an open proximal extremity 22, defining a central lumen 24. The dimensions of the stent will depend on the anatomy of the patient. For many applications, the preferred stent has an outside diameter of between about 0.010 inch and 0.070 inch, and typically about 0.030, an internal diameter of between about 0.006 inch and 0.065 inch, and typically about 0.021 inch, and a length of between about 4 and 15 inches, typically about 6 inches, or typically just an inch or two longer than the sleeve.

The sleeve 30 has an open distal end 31, an open proximal end 32 and an internal axial channel 34. The distal end 31 of the sleeve is preferably blunted, having a rounded rim 33 which facilitates insertion into the lacrimal structures. An optional flange 36 extends radially outwardly from the proximal end of the sleeve in order to prevent over-insertion into the lacrimal system and to provide a grasping point for withdrawl of the sleeve over the stent.

The preferred material of the sleeve 30 is any durable, biocompatible, semi-rigid material such as ULTEM brand plastic material available from General Electric Company of Fairfield, Conn. Other acceptable materials include Nitinol, stainless steel, titanium, silver, aluminum, bronze, brass or any alloy of these metals, or of synthetic materials such as polypropylene, PEBEX, Kevlar, polymide, Dacron, nylon, EPTFE or PVC or other material known to those skilled in the art.

The inner diameter $D_G$ of the sleeve 30 is selected to allow it to be intimately engaged by the stent 20 having a given cross-sectional dimension $D_S$ perpendicular to its elongation axis $A_S$. The dimensions of the sleeve will depend on the anatomy of the patient. For many applications, the preferred sleeve has an outside diameter of between about 0.014 inch and 0.060 inch, and typically about 0.038 to 0.040, an internal diameter of between about 0.010 inch and 0.046 inch, and typically about 0.031 to 0.032 inch, and a length of between about 1 and 15 inches, typically about 4 inches. This translates into a wall thickness of between about 0.002 and 0.020 inch, and typically about 0.002 to 0.005 inch. (Those skilled in the art will appreciate that subtracting the inner diameter from the outer diameter results in 2 times the thickness). Depending on the embodiment and application, the sleeve can have a luer lock or other connector on its proximal end and may have a handle on its proximal end or mid-section (not shown). Although the sleeve is made of a rigid or semi-rigid material, its length and the relative thinness of its wall may render it quite flexible and easily bendable.

In order to increase the flexural rigidity of the combined sleeve/stent structure, a stiffening rod 40 such as a surgical probe, having a rounded distal terminus 41 is selected to coaxially engage the lumen 24 of the stent and thereby engage the channel 34 of the sleeve 30. Therefore, the outside diameter of the rod is slightly smaller than the inside diameter of the stent.

The distal terminus 41 of the rod contacts the closed distal extremity 21 of the stent. The length of the rod is at least as long as the stent, and more preferably between about 0 and 25 centimeters longer than the stent. In most applications its is convenient to have the rod be about 10 centimeters longer than the stent.

The rod can be made of stainless steel, Nitinol or other similar material known in the art. A manipulable flattened or otherwise enlarged section at or near the proximal end of the rod, as can be found in many surgical probes, facilitates its handling.

The rod 40 can be hollow having an internal tunnel 44 extending from an open (not shown) or closed distal terminus 41 an open proximal terminus 42 having a connector 43 such as luer-lock. The diametric width $W_C$ of the connector can be selected to be smaller that the inside diameter of the sleeve 30 so that the sleeve can be withdrawn over the connector. Alternately, the length of the rod can be selected so that the while the rod remains inserted in the lacrimal drainage system, the sleeve can be fully withdrawn from the system, but not over the connector as will be described below in reference to FIG. 7.

A first radial hole 45 punctures through the cylindrical wall of the rod 40 close to the distal terminus. This hole 45 is located near a second radial hole 25 puncturing through the cylindrical wall of the stent 20, which in turn, is located near a third radial hole 35 puncturing through the cylindrical wall of the sleeve 30. These holes allow for the injection of fluid, or potentially the suction of debris through the combined structure. The holes are located proximal to the distal extent of the combined structure so that if the open distal end 31 of the sleeve 30 is blocked by the nasal floor 11, there will still be an open exit port from which fluid can escape. The holes can be aligned with one another by using marks or other indicators on the rod, stent and sleeve. Alternately, the holes can remain out of alignment relying on the fluid pressure to force its way through the holes successively.

Stent Insertion

Figure 4:
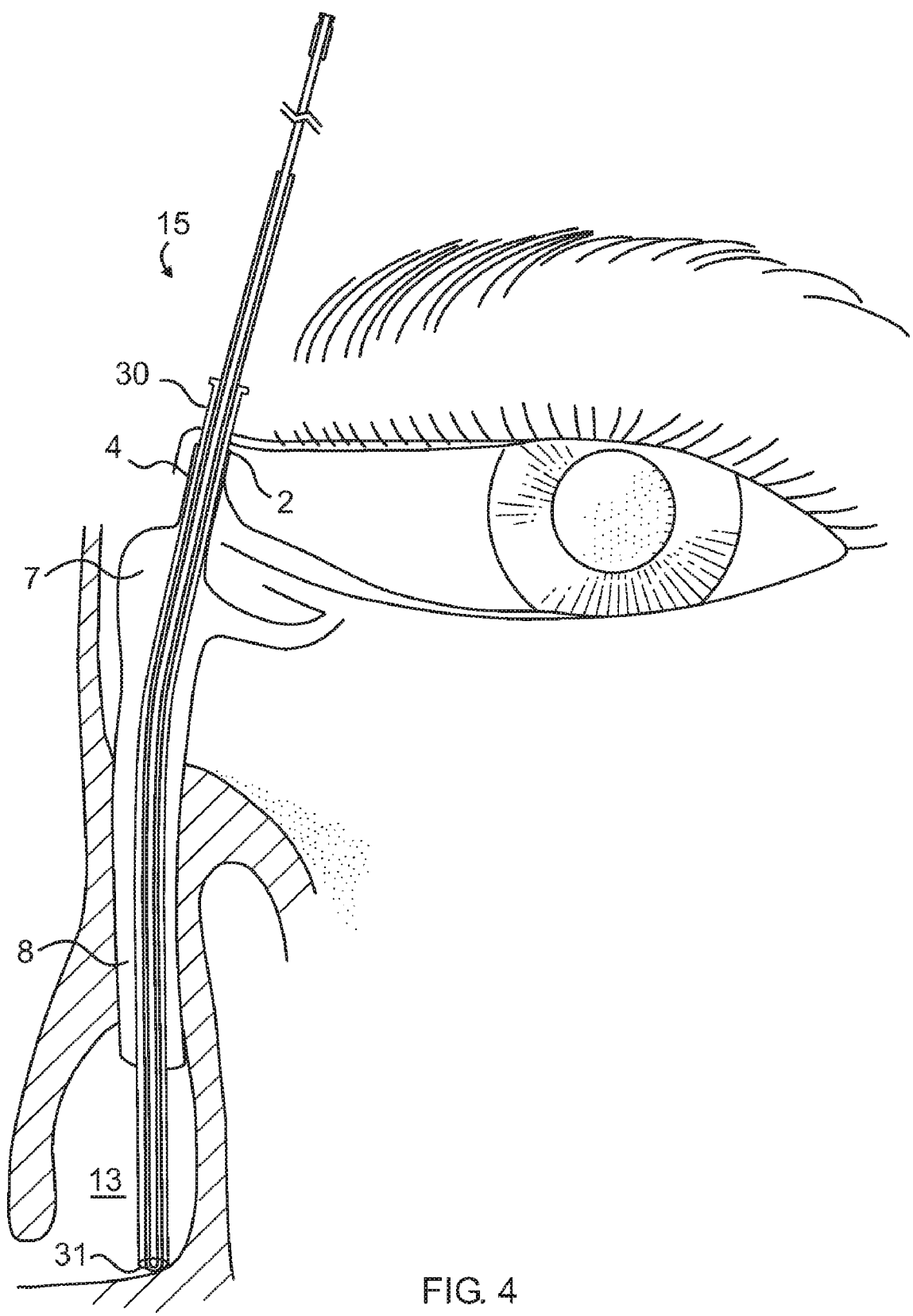
FIG. 4 illustrates a stiffening rod inserted into the stent and guide sleeve to facilitate insertion.

Referring now to FIG. 4, there is shown a cross-sectional view of a portion of a human patient's nasolacrimal drainage system showing the combined sleeve/stent structure 15 inserted. In order to emplace the combined sleeve/stent structure, the distal end 31 of the sleeve 30 is inserted horizontally through the punctum 2 and canaliculus 4 into the lacrimal sac 7. The sleeve is then oriented vertically and pushed down the nasolacrimal duct 8 into the nasal cavity 13 out the duct opening into the nasal cavity until it hits the nasal floor. The duct in the drawing which is shown in an expanded state for clarity. Typically, the duct would closely conform to the sleeve. In this example the sleeve is inserted into the superior punctum and canaliculus, but would work similarly in the inferior punctum and canaliculus.

A suction procedure can be performed through the combined stent/sleeve structure. Further, after disconnecting the suction device, irrigation may be performed. The combined stent/sleeve can also be used at that time to deliver medications into the various parts of the lacrimal drainage system that the tip of the structure passes through. In addition, the combined stent/sleeve can be connected to a source of lubricant that can be injected to ease the penetration of the stent/sleeve.

Figure 5:
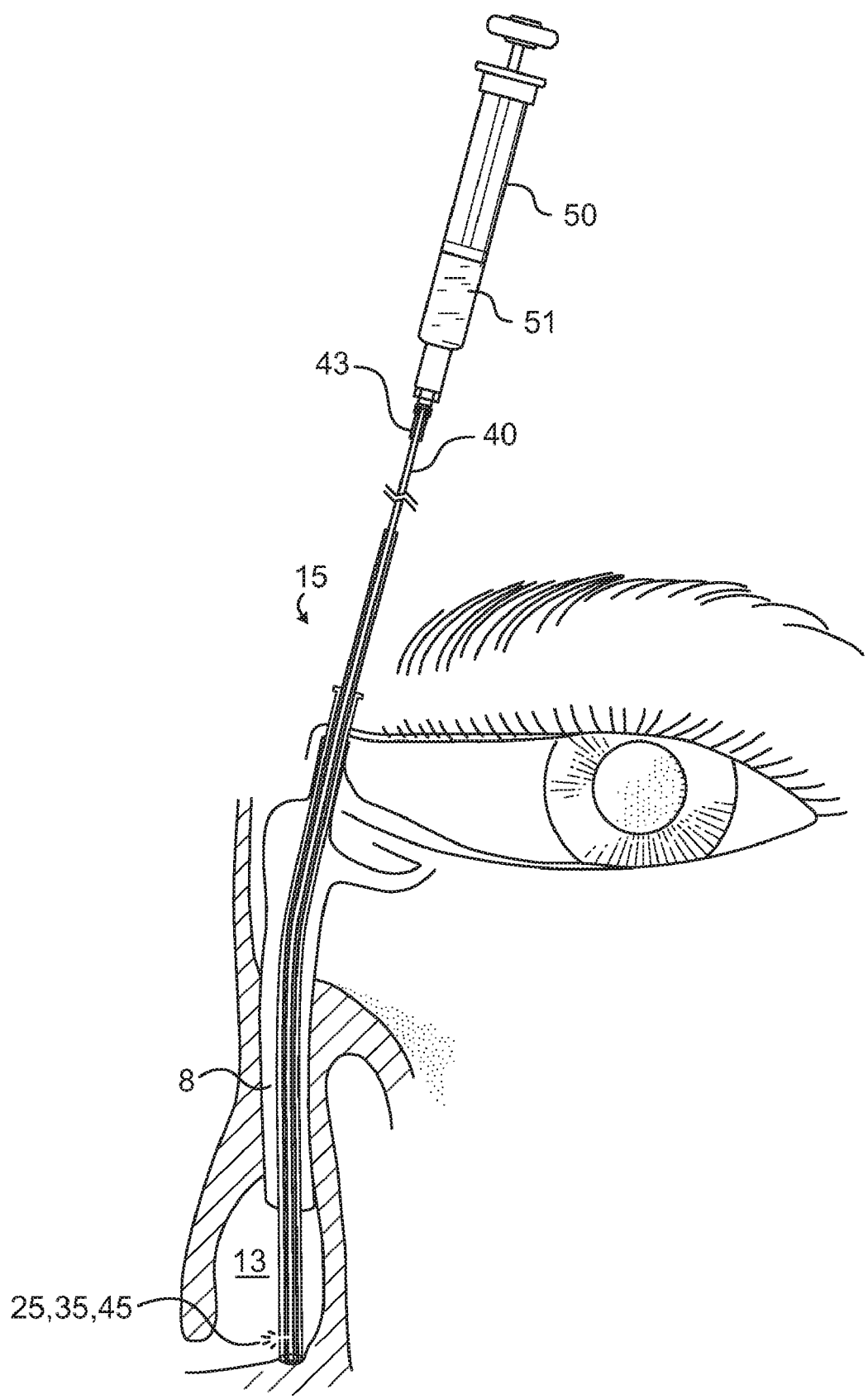
FIG. 5 illustrates injection of a tracing fluid to verify the location of the distal end of the guide sleeve.

As shown in FIG. 5, the surgeon must then confirm that the structure 15 has penetrated all obstructions in the nasolacrimal duct 8 and reached the nasal cavity 13. Confirmation can be made without visualization in the nasal cavity and without contacting the distal end of the sleeve in the nasal cavity using another instrument. Instead, proper placement is confirmed by connecting a syringe 50 filled with fluorescein-stained fluid 51 to the proximal luer-lock connector 43 on the rod 40. Fluid is then injected through the rod and out the holes 25,35, 45. The fluid can be suctioned out of the nasal cavity 13 with a soft suction or other suction catheter. If the fluorescein-stained fluid irrigates easily and a large volume is suctioned out of the nose, this indicates that the combined stent/sleeve structure has penetrated all obstructions and stenoses and entered the nasal cavity. Otherwise, it is likely that the guide has not adequately penetrated or has followed a false passage. In this case, the combined stent/sleeve must either be pushed further down the nasolacrimal duct into the nasal cavity, or the combined stent/sleeve must be pulled proximally until its tip is in the lacrimal sac, reoriented and pushed down again through the nasolacrimal duct into the nasal cavity. The same irrigation and suctioning procedures are repeated as describe above until proper penetration has been confirmed.

It will be clear that in the combined stent/sleeve structure where the rod and stent are engaged in the channel of the sleeve, pressurized fluid passing through the tunnel of the rod can be said to be passing through the lumen of the stent, and can be said to be passing through the channel of the sleeve.

Figure 6:
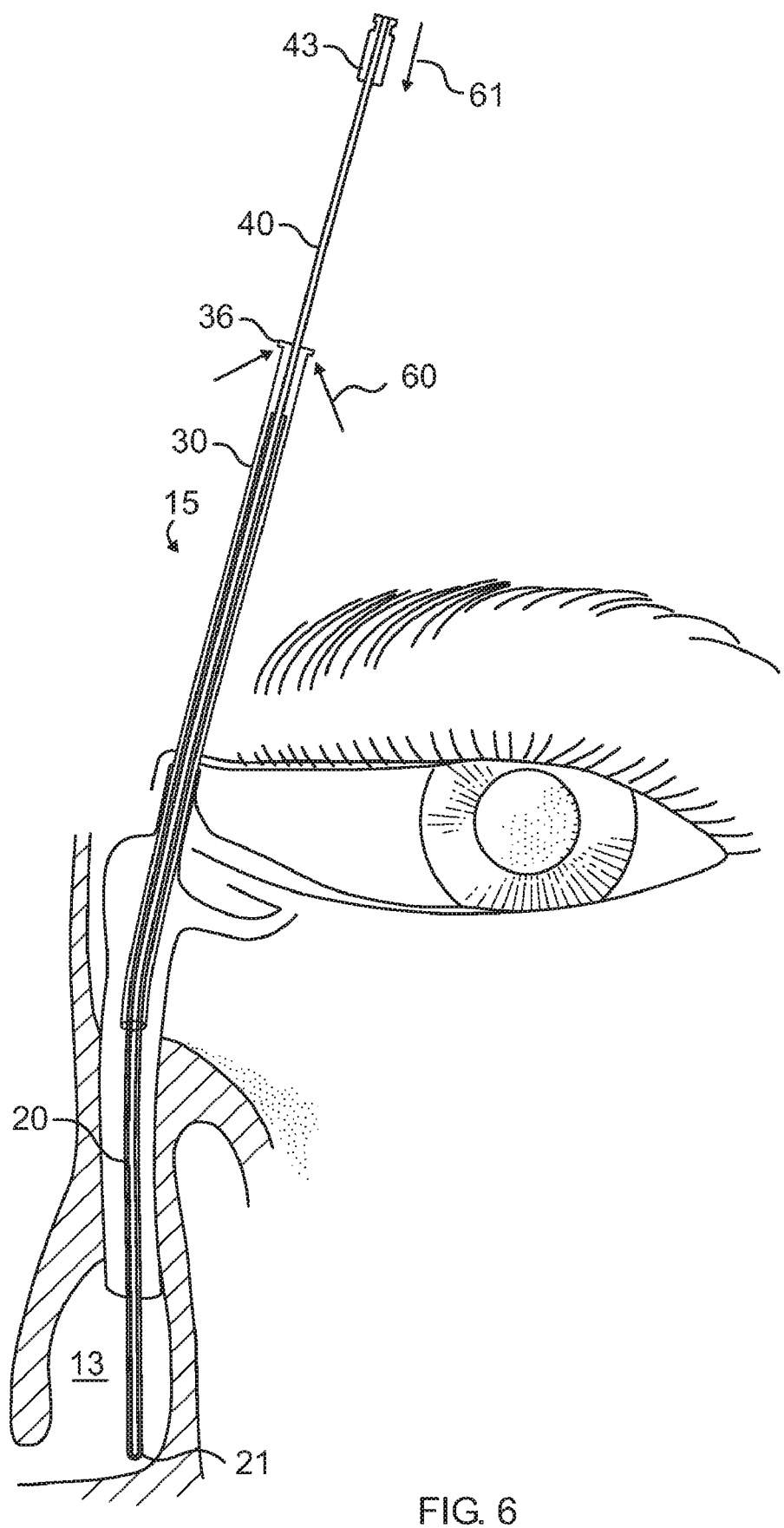
FIG. 6 illustrates the guide sleeve being withdrawn from the stent mounted on the rod.

As shown in FIG. 6, once the combined stent/sleeve structure 15 is confirmed emplaced, and while the stent 20 remains mounted upon the stiffening rod 40, the sleeve 30 can be withdrawn out the punctum from the lacrimal drainage system by applying a withdrawing force 60 on the proximal flange 36 of the sleeve while simultaneously applying a balancing, inserting force 61 on the rod. This causes the sleeve 30 to move proximally with respect to the substantially stationary stent/rod so that the stent remains in place with its distal end 21 in the nasal cavity 13.

Figure 7:
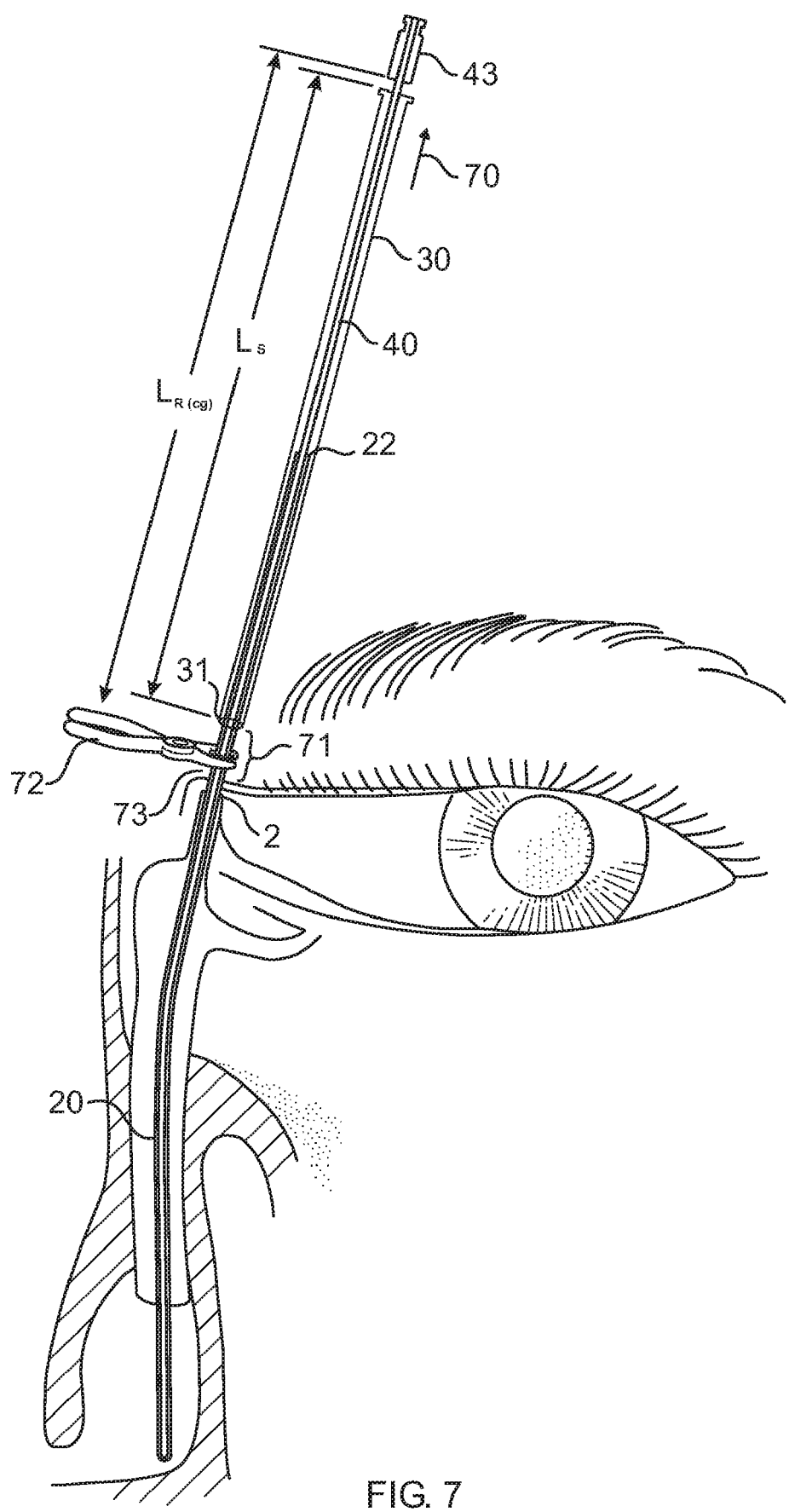
FIG. 7 illustrates the grasping of the stent near the punctum while the sleeve and rod are withdrawn from the lacrimal system.

As shown in FIG. 7, the sleeve 30 is further pulled proximally 70 and upward out of the lacrimal drainage system until the distal end 31 of the sleeve is just outside the lacrimal system, a few millimeters proximal from the punctum 2. A middle section 71 of the stent 20 located adjacent to the punctum is then gently grasped using a grasping instrument 72 such as a needle holder or forceps at a grasping point 73 just proximal to the punctum. The stent is thereby held in place in the lacrimal system and nasal cavity while the sleeve and rod are further withdrawn proximally and removed completely by being pulled off the proximal end of the stent.

Since the connector 43 is too large to fit through the channel of the sleeve, the length of the rod 40 is selected so that the length $L_{R(cg)}$ from the connector to the grasping point 73 is longer than the length $L_S$ of the sleeve. Alternately, if the connector is small enough to fit through the channel of the sleeve, the surgeon can remove his or her hand from the proximal end of the stiffening rod so that the proximal end of the guide can be withdrawn over it. The surgeon continues to hold the stent 20 using a grasping instrument 72 adjacent to the punctum 2. The stiffening rod 40 is then pulled out the proximal end 22 of the tubular stent and completely withdrawn.

Figure 8:
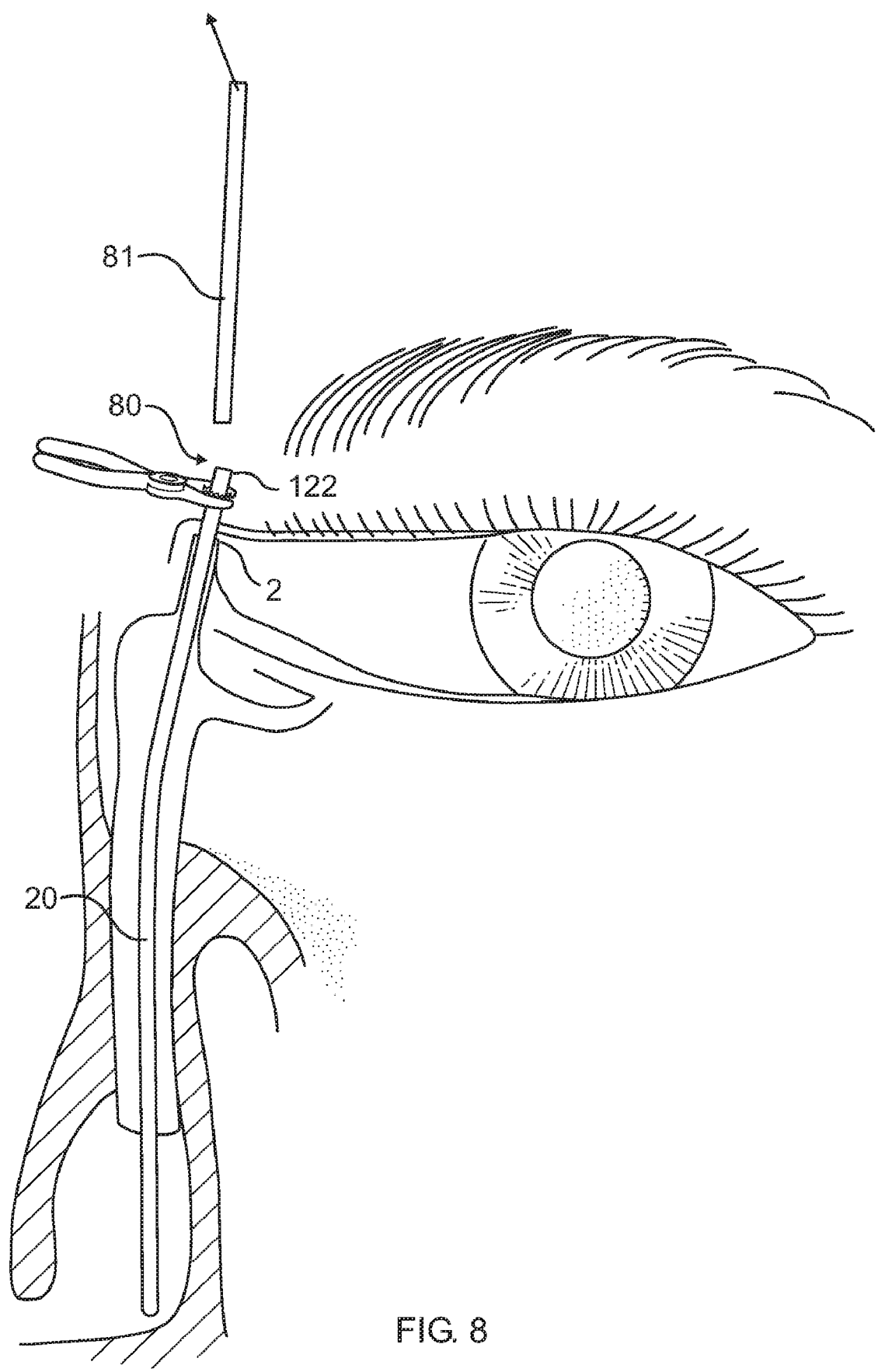
FIG. 8 illustrates removal of excess proximal portion of the stent.

As shown in FIG. 8, the stent 20 as emplaced is longer than needed, so it is now cut at a point 80 about one to two centimeters proximal from the punctum 2 thereby separating an excess proximal section 81 which is discarded, forming a new proximal extremity 122 on the now shortened stent.

Alternate Stent Insertion Using Guide Sleeve

The stent can be similarly emplaced up to this point using an alternate method described with reference to FIGS. 9-13 where the sleeve is first separately emplaced as a tubular guide with or without the aid of a stiffening rod depending on the needed flexural rigidity. Once placement is confirmed the stent/rod is threaded through the sleeve.

Figure 9:
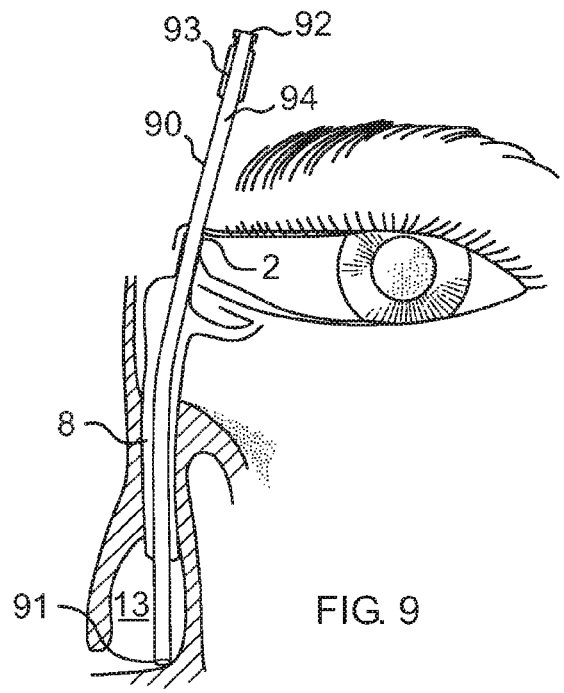
FIG. 9 illustrates placement of the guide sleeve using an alternate method.

Referring now to FIG. 9, there is shown a cross-sectional view of a portion of a human patient's nasolacrimal drainage system showing an elongated tubular guide sleeve 90 (or simply "guide") similar to the type shown in the previous embodiment having an open blunted distal end 91, an open proximal end 92 and an internal axial channel. The guide has been inserted similarly through a punctum 2, then down through the lacrimal duct 8 and into the nasal cavity 13. One primary difference in this embodiment is that the guide sleeve itself has the proper range of flexural rigidity to be inserted in the lacrimal drainage system. Therefore the preferred range of flexural rigidity is similar to that of the combined stent/sleeve/rod of the previous embodiment. As shown below, that rigidity can be achieved by the temporary insertion of a rigidizing rod such as a surgical probe through the channel of the guide prior to insertion into the lacrimal system. Once inserted the rod can be withdrawn from the sleeve.

Another important difference is the guide 90 has a luer lock or other connector 93 on its proximal end 92 for the connection of a source for fluid injection or suction, and may have an additional handle on its proximal end or mid section (not shown).

Figure 10:
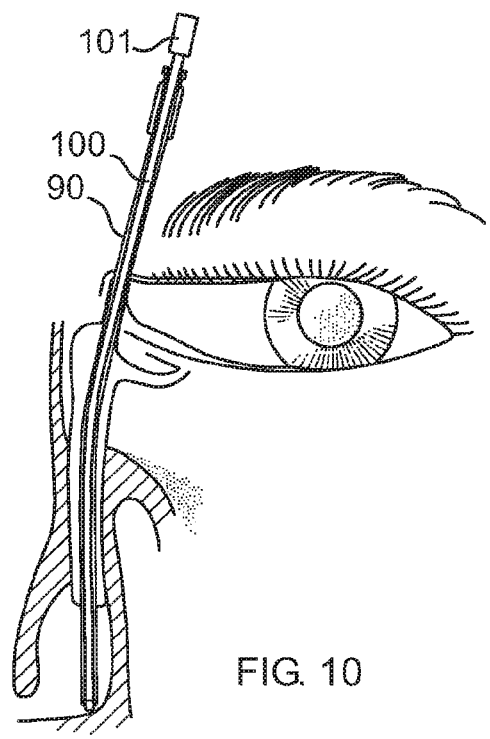
FIG. 10 illustrates placement of the guide sleeve using a rigidizing rod.

As shown in FIG. 10, to temporarily increase the flexural rigidity of the guide 90 during insertion, a stiffening rod 100 diametrically sized to engage the channel of the guide is used. The rod has a length slightly in excess of the total length of the tube, and can be made of stainless steel, Nitinol or other similar material known in the art. A manipulable flattened or otherwise enlarged section 101 at the proximal end of the rod facilitates its handling. Use of the rod further allows for the use of a guide sleeve having a thinner wall, which is typically less than 90%, often less than 75%, and sometimes even less than 50% of the thickness required when no rod is present. A thinner wall reduces material cost, and provides a less intrusive cross-section.

Figure 11:
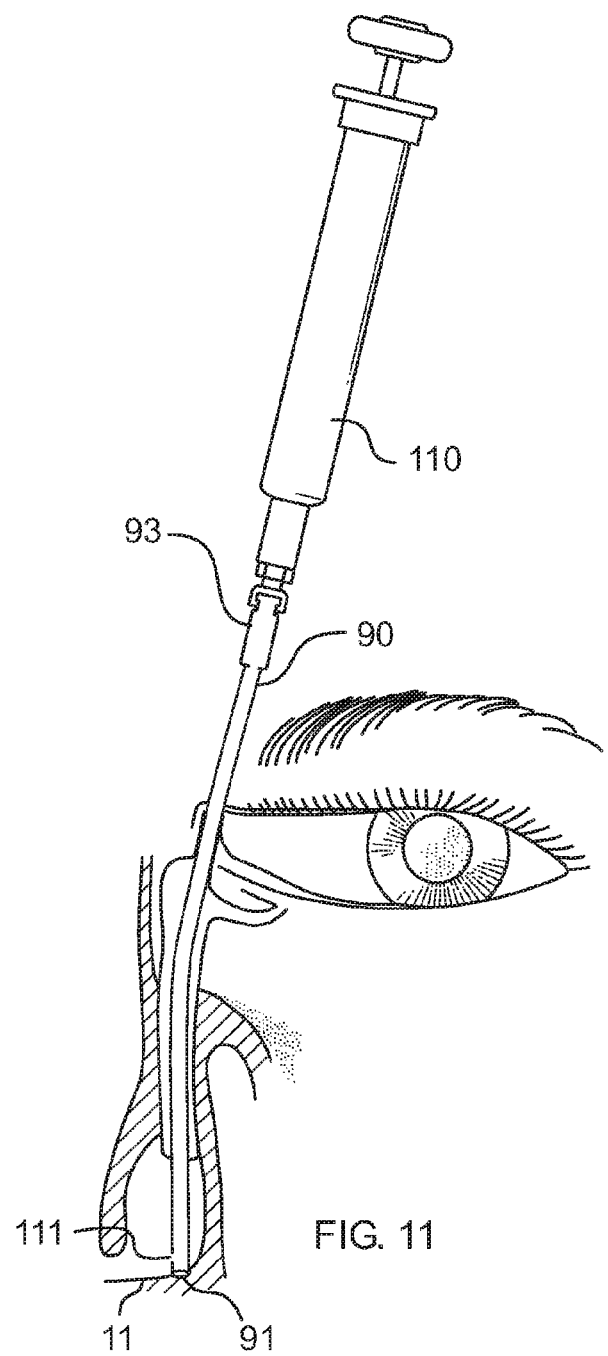
FIG. 11 illustrates irrigation of fluorescein-stained fluid through the guide sleeve.

As shown in FIG. 11, placement of the guide is confirmed by connecting a syringe 110 filled with fluorescein-stained fluid to the proximal luer-lock connector 93 on the tubular guide 90. Fluid is then injected through the guide to determine whether the guide is properly placed according to the procedure describe in the previous embodiment. Further the guide can be formed to have a radial hole 111 near the distal end 91 to allow fluid flow when the axial opening at the distal end is blocked by the nasal floor 11 or other structure. After confirmation, the syringe is detached from the guide.

It shall be clear that if a rigidizing rod is used to stiffen the guide during insertion, a hollow rod can be selected having its own luer lock connector and radial distal exit hole through which the fluid can be injected while the rod is still engaged with the guide.

Figure 12:
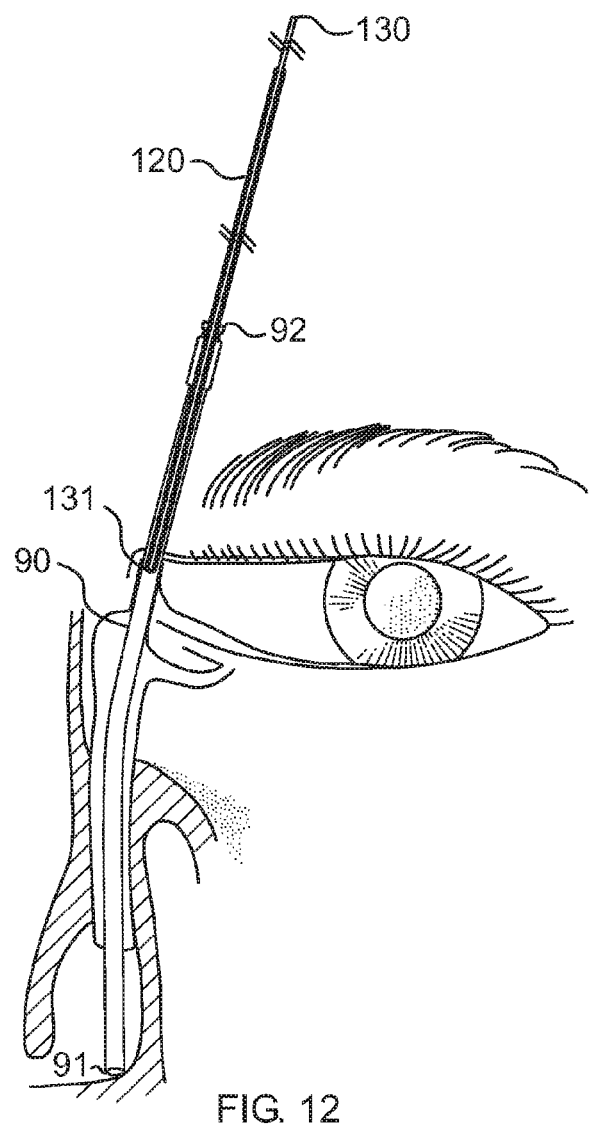
FIG. 12 illustrates the stent mounted to a rigidizing rod being inserted into the placed guide sleeve.

Referring now to FIG. 12, an elongated stent 120 is selected by the surgeon to be threaded through the guide 90. The preferred stent is similar to the type shown in the previous embodiment having an closed blunted distal end, an open proximal end and an internal axial lumen, and formed from a length of flexible tubing made from a biocompatible material such as silicone, polyethylene, or other material known to those skilled in the art.

The tubular stent is temporarily coupled to a stiffening rod 130 such as a surgical probe having a rounded distal end 131. The rod is inserted into the stent until its distal end contacts the closed distal end of the stent. The length of the rod is at least as long as the stent, and more preferably between about 0 and 25 centimeters longer than the stent. In most applications its is convenient to have the rod be about 8 centimeters longer than the stent.

The temporarily stiffened stent is now introduced into the proximal end 92 of the guide 90 and pushed down the guide while grasping only portions of the stent extending from the proximal end of the guide. The combined stent and rod will have sufficient rigidity and column strength to allow it to be pushed through the guide. However, the combined stent and rod will have sufficient flexibility to easily follow the guide around the bends and angles in the lacrimal system. It should be made clear that the guide sleeve therefore has an unobstructed central channel having sufficient rigidity and continuity to allow the pushing of the stent through the channel using only forces applied to the stent on portions of the stent or stent/rod combination extending from said proximal end of said guide sleeve.

Figure 13:
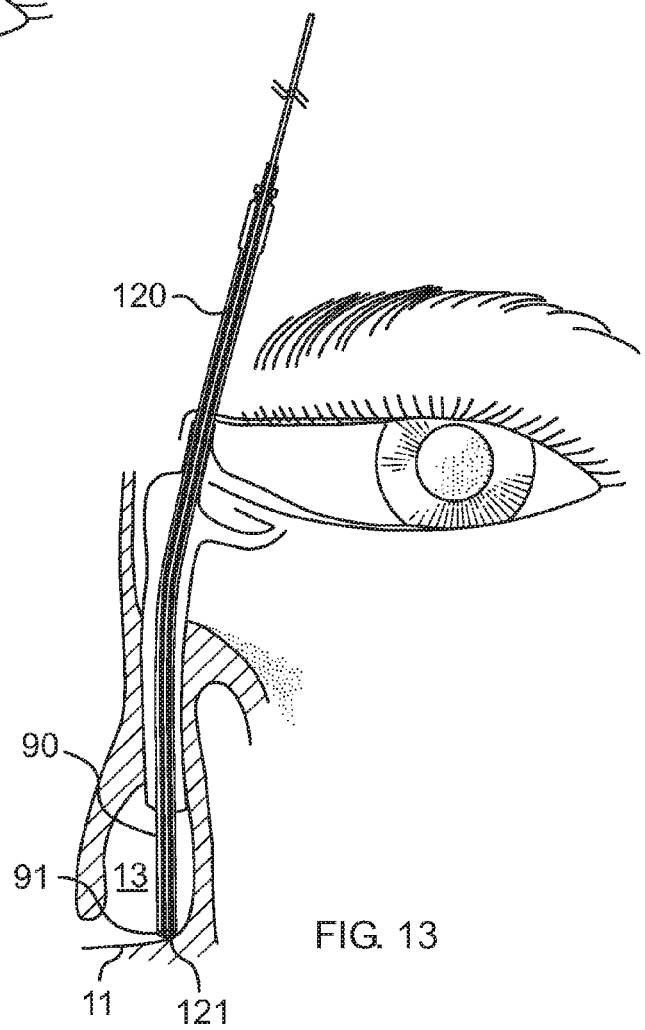
FIG. 13 illustrates the distal extremity of the stent reaching the distal end of the guide sleeve.

As shown in FIG. 13, the pushing of the stent 120 continues until the stent comes to the distal end 91 of the guide 90 in the nasal cavity 13. The surgeon may feel resistance to further penetration when the distal end 121 of the stent comes into contact with structures, such as the nasal floor 11, residing outside the distal end of the guide. It shall be appreciated that the stent is easily pushed through the channel of the guide. Only mild pressure is needed and thus there is no danger of penetration of the distal end of the stent by the stiffening rod. Also, there is no need to confirm that the stent is emplaced.

It is important to note that the guide allows smooth placement of the stent with far less force than would be required without the guide. Thus, no reinforcement is needed at the distal tip of the stent to prevent puncturing by the rod.

Finally, the guide and then the rod are withdrawn according to the procedure described in connection with the previous embodiment. Then the stent length is trimmed from the proximal end.

Anchoring the Stent to the Punctum

Figure 14:
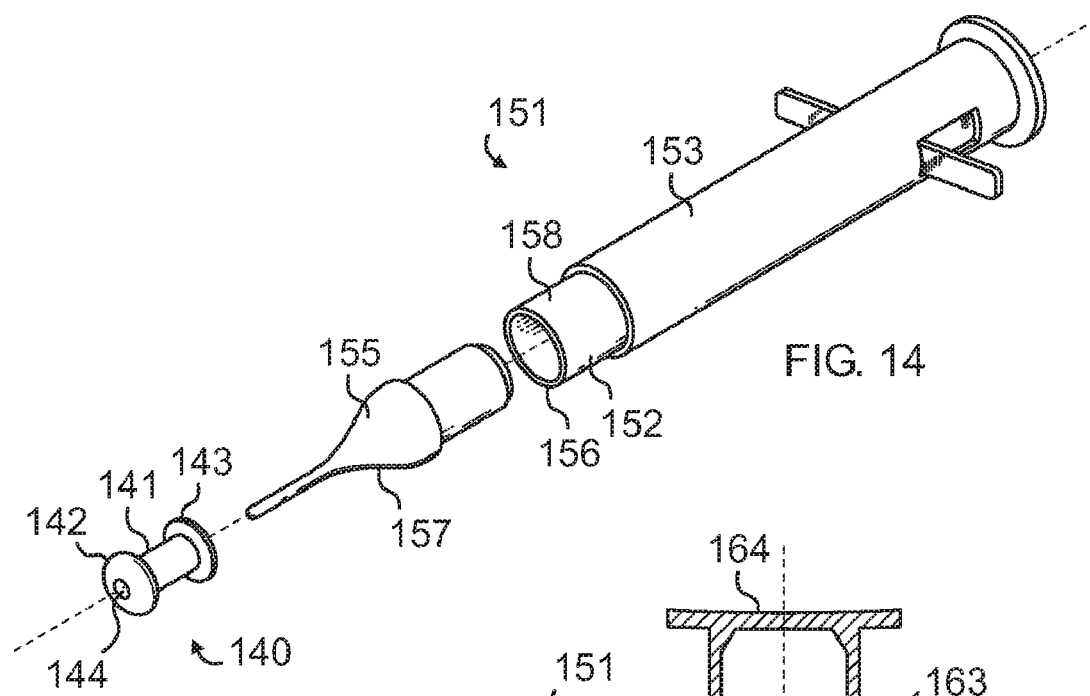
FIG. 14 is a perspective view of a punctal anchor and introducer device.
Figure 15:
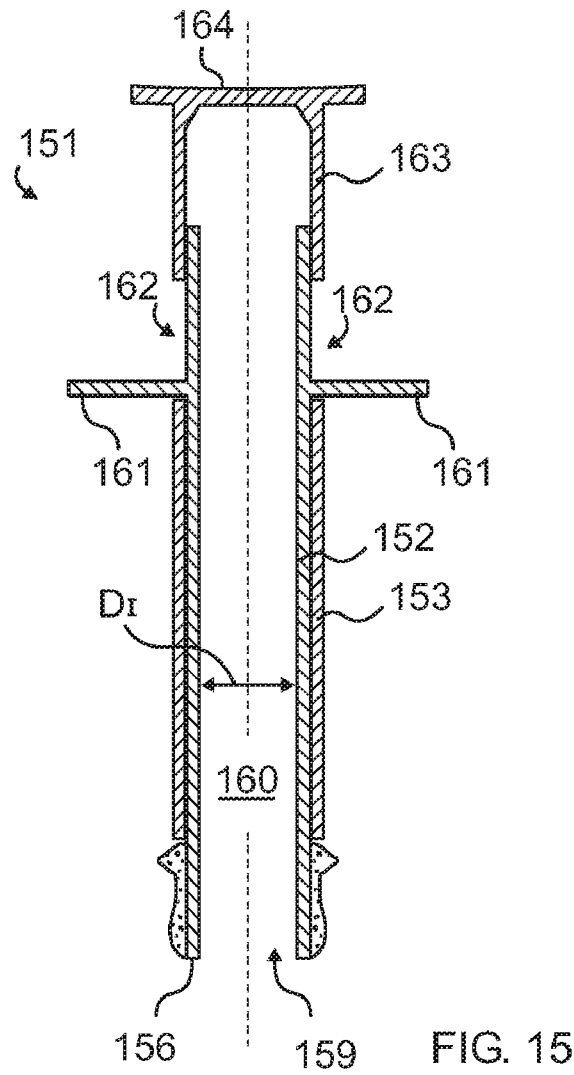
FIG. 15 is an illustrative cross-sectional view of the introducer and anchor mounted thereon.

Referring now to FIGS. 14-15, there is provided a radially expandable punctal anchor 140 sized and shaped to be affixed to the proximal end of the emplaced stent and pushed into place in a patient's punctum, thereby anchoring the stent the punctum. The preferred anchor is made from a unitary piece of flexible, resilient bio-compatible material such as silicone, but may be made of polypropylene or other material familiar to those skilled in the art. An anchor sized to intimately and oversizedly engage the punctum in the presence of a portion of the flexible stent.

The punctal anchor has a generally cylindrical shaft 141 having a widened distal end 142 and a proximal end formed into a flange or collar 143. The anchor has an axial length of between about 0.2 and 8 mm, and is typically between about 2.0 and 2.5 mm for most adult human patients. The shaft 141 has a resting outside diameter which allows it to fit comfortably in the punctum and adjacent portion of the canaliculus, this diameter will depend on the anatomy of the patient and is preferably between about 0.1 and 3.0 mm, and is typically between about 0.7 and 1.0 mm for most adult human patients, the average diameter is ideally about 0.9 mm.

The widened distal end 142 of the anchor forms a rounded protuberance having a larger diameter which, when at rest, is preferably slightly oversized than the patient anatomy so that it forms a friction fit to keep the anchor from extruding. The outer diameter of the protuberance is preferably between about 0.021 and 4 mm, and is typically between about 1 and 2 mm for most adult human patients, the average diameter is ideally about 1.5 mm.

The collar 143 keeps the anchor from migrating internally when the anchor is emplaced. Thus the collar is sized, shaped and located to rest against the lid margin just external to the punctum. Therefore, the collar has an outer diameter which is large enough to keep it from migrating into the punctal lumen, but small enough to avoid irritating the eye. The outer diameter of the collar will depend on the anatomy of the patient and is preferably between about 0.020 and 4 mm, and is typically between about 1.5 and 2.5 mm for most adult human patients, the average diameter is often ideally about 1.75 mm.

The punctal anchor has a very small, open-ended cylindrical bore 144 sized to fit over and snugly engage the proximal end of the stent forming a friction fit thereto. Therefore, the resting diameter of the bore is smaller than the cross-sectional dimension $D_S$ of the stent. Although the bore is shown penetrating the anchor axially, the bore could penetrate from other directions, for example radially.

The punctal anchor 140 is affixed to the stent through means of an introducer 151. The introducer has a generally cylindrical inner tubular body 152 slidingly and telescopingly engaging an outer tubular sheath 153. The body is made from a durable, rigid material such as nitinol, stainless steel, plastics or other material known to those skilled in the art.

The anchor is stretched onto the inner body 152 using a rounded flaring spike 155 which temporarily mounts onto the distal end 156 of the body. As the anchor is pushed in the proximal direction onto the spike, the gradual flaring of the outer surface 157 of the spike causes the anchor to expand and fit over the distal outer surface section 158 of the body 152. The outer diameter of the outer surface section 158 of the body is preferably between about 0.3 and 6 mm, and is typically between about 2 and 3 mm for most adult human patients, the average diameter is ideally about 2.5 mm and is commensurate with the widest outer diameter of the spike, and to stretchingly engage the bore of the anchor. After the anchor has been stretched onto the distal end of the body, the spike 155 is removed, as shown in FIG. 15.

The inner body 152 of the introducer has a distal opening 159 leading to a cylindrical internal cavity 160. The inner diameter $D_I$ of the cavity is selected to be larger than the cross-sectional dimension $D_S$ of the stent 30 so that the proximal end of the stent can easily fit into the cavity during affixation of the anchor as detailed below. Therefore, inner diameter of the cavity is preferably between about 0.2 and 5.5 mm, and is typically between about 1.75 and 2.75 mm for most adult human patients, the average diameter is ideally about 2.25 mm. A pair of gripping prongs 161 extend radially from opposite sides of a proximal section of the inner body through a pair of slots 162 formed through the sidewall 163 of the sheath 153. The sheath has a proximal thumb rest 164. The two gripping prongs are sized, shaped and located to provide for comfortable and precise manipulation by the surgeon. Therefore, although the angular size of each prong can be between about 1 and 90 degrees of arc, it is most preferably about 30 degrees.

Figures 16, 17:
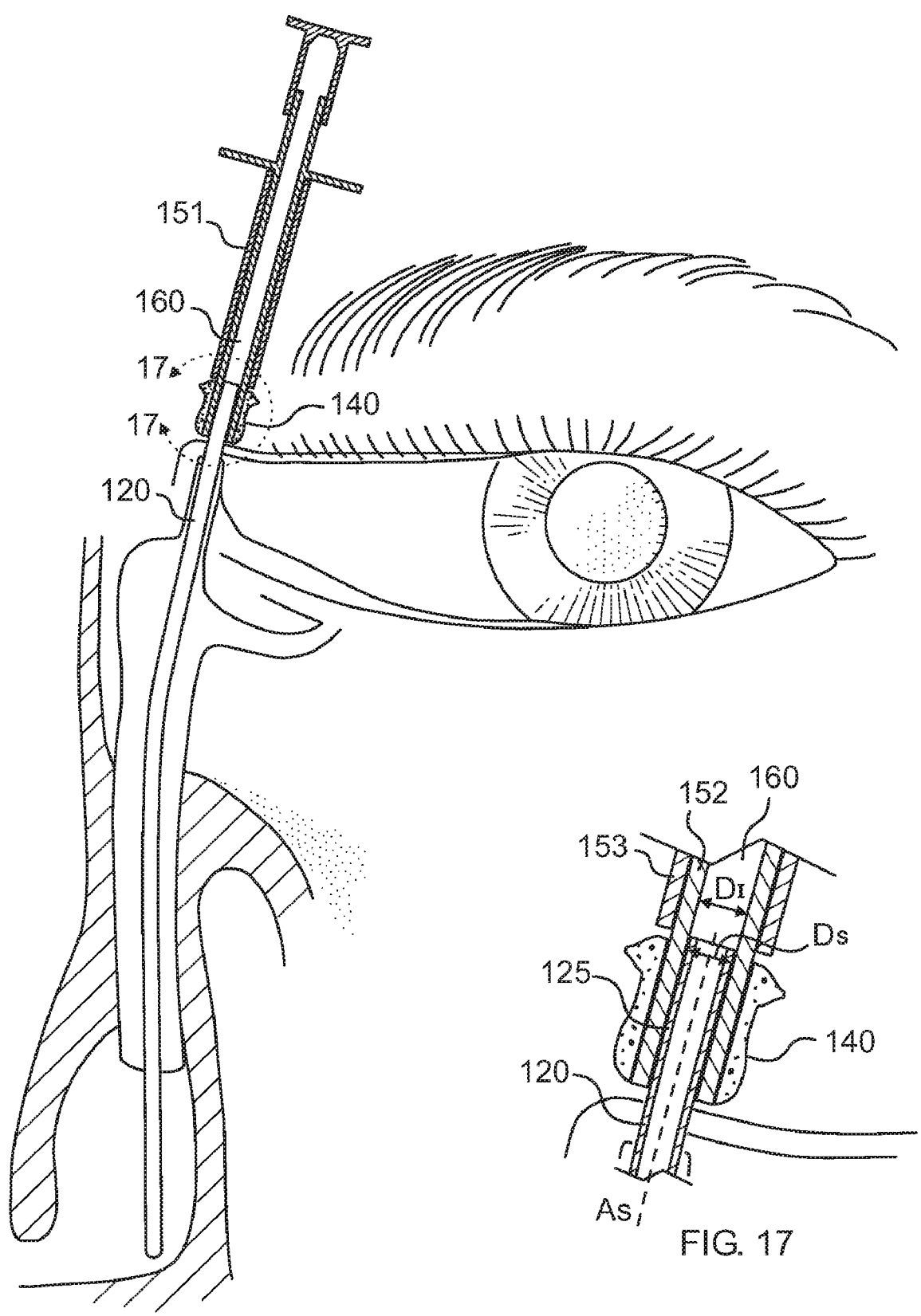
FIG. 16 illustrates the threading of the introducer onto the proximal end of the stent tube.
FIG. 17 is an enlarged view of the illustration of FIG. 16 taken within curve 17-17.

As shown in FIGS. 16 and 17, the introducer 151, having a punctal anchor 140 mounted on its distal end, is now brought over the new proximal extremity and proximal portion 125 of the shortened emplaced flexible stent 120 such that the stent threads into the cavity 160 of the introducer. The introducer is pushed in a distal direction until it touches the punctum.

Figure 18:
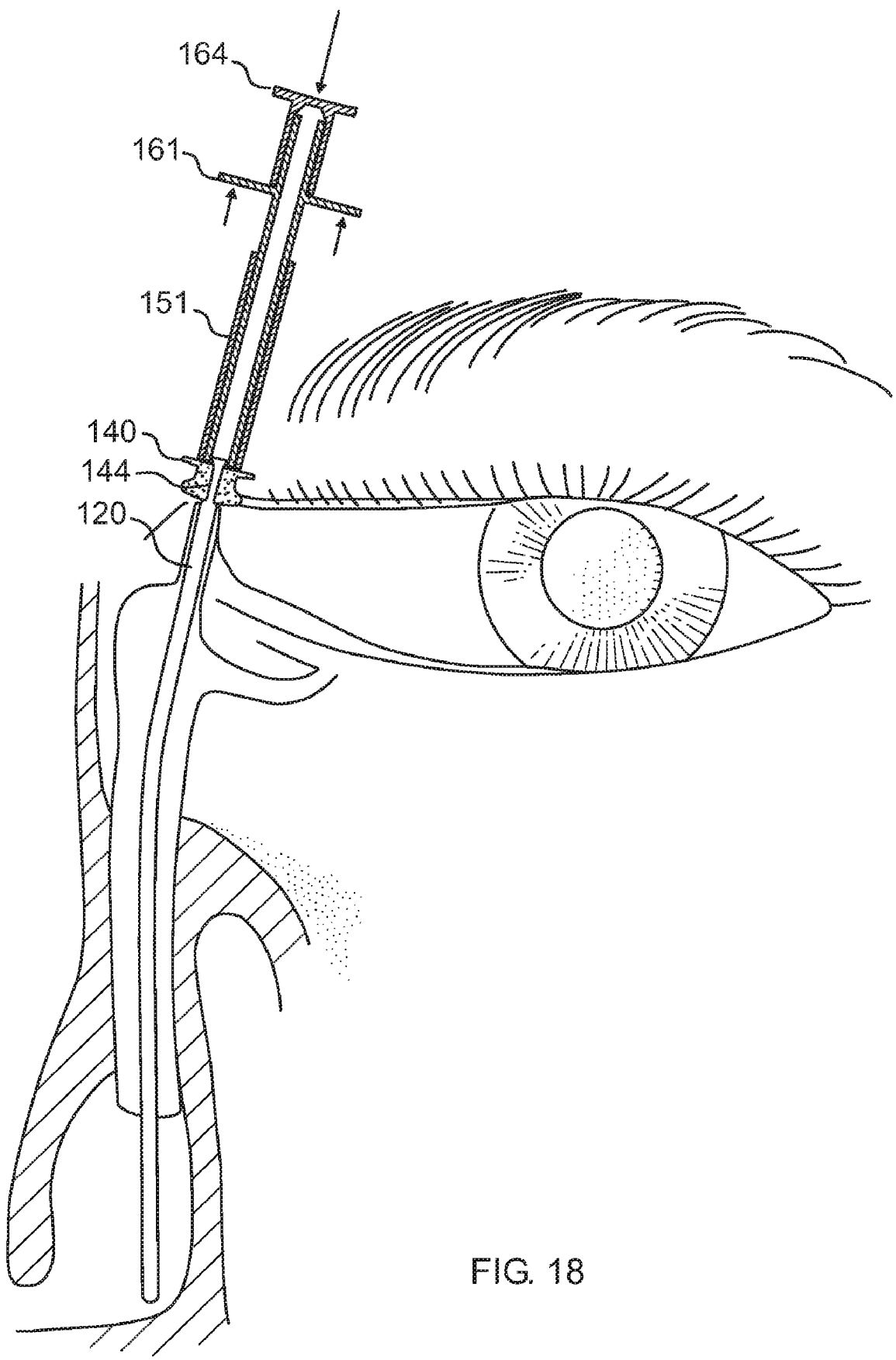
FIG. 18 illustrates the placement of the anchor onto stent tube near the superior punctum.

As shown in FIG. 18, the anchor 140 is now released from the introducer 151 onto the stent 120 by the surgeon squeezing the thumb rest 164 toward the gripping prongs 161. This causes the distal end of the sheath to bear against the collar of the anchor, and force the anchor off the distal end of the inner body. The resiliency of the anchor causes its bore 144 to collapse and clamp down onto the proximal portion of the flexible stent which also collapses under the force of the contracting anchor, causing a friction fit therebetween.

Figure 19:
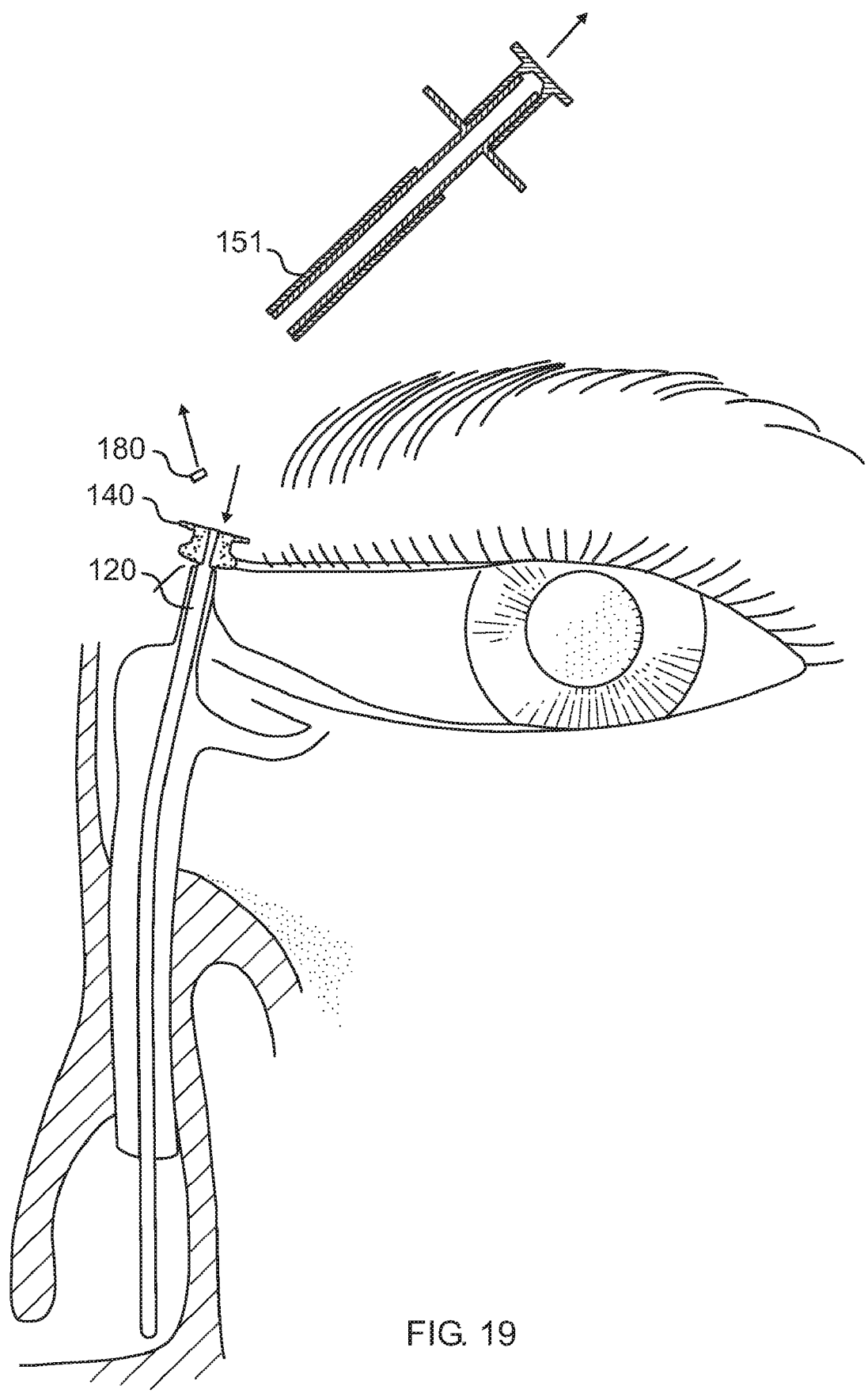
FIG. 19 illustrates removal of excess stent tube proximal the emplaced anchor.

As shown in FIG. 19, the introducer 151 is removed proximally. The proximal part of the stent 120 is cut flush with the proximal end of the anchor 140 and the excess stent 180 removed.

Figure 20:
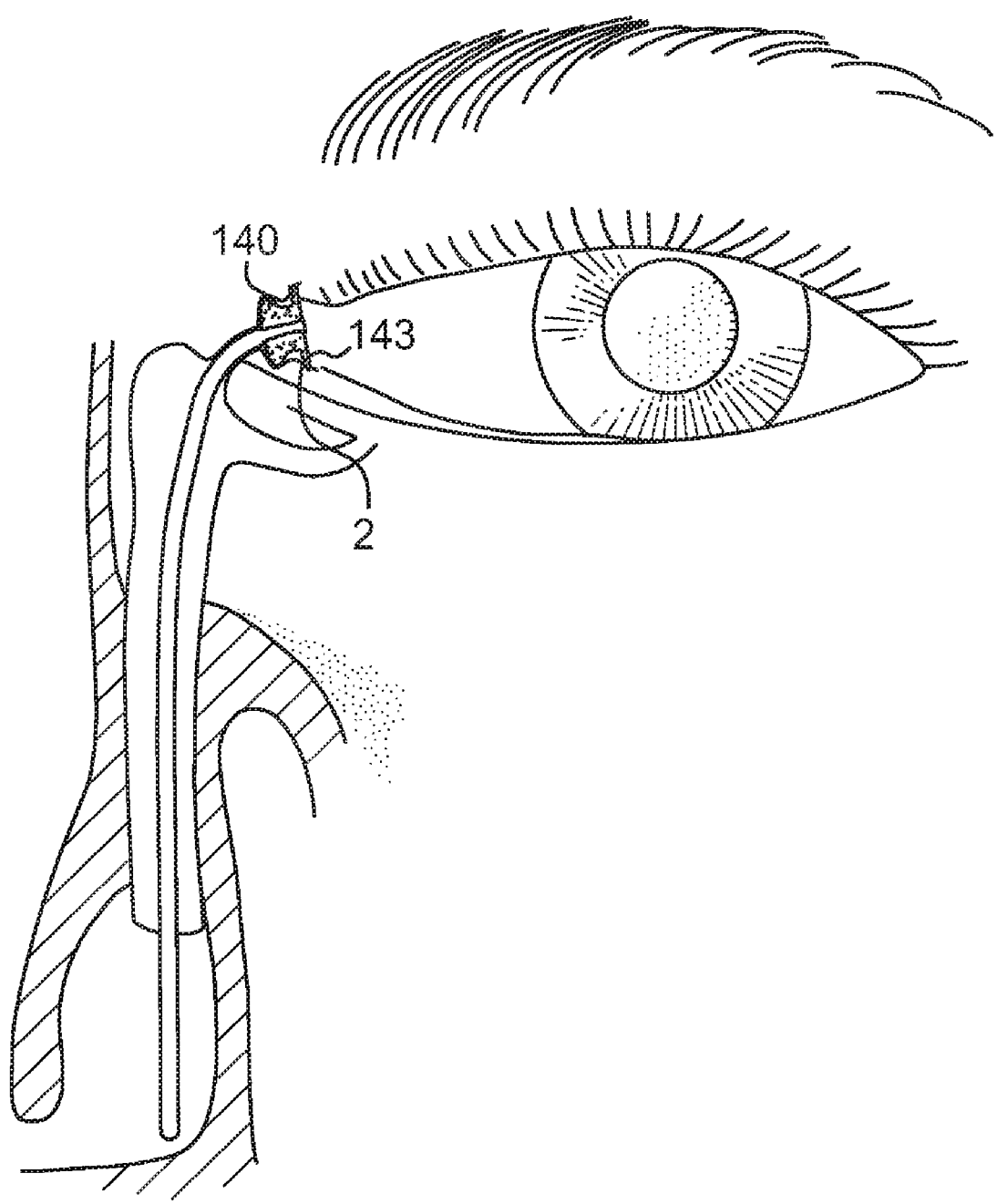
FIG. 20 illustrates stent tube finally seated within the lacrimal system and anchored by the punctal anchor.

As shown in FIG. 20, the anchor 140 is then pushed distally into the punctum until the collar 143 rests against the outer rim of the punctum 2.

Thus, only one length of stent is needed, since the surgeon can cut the proximal end to the desired size during each surgery. Unlike prior devices and methods, placement of the stent can be accomplished in absence of visualization and in absence of retrieval of the stent in the nose. Further, placement is accomplished in absence of any shortening of the distal end of the stent. In other words the surgeon does not need to visualize or use any additional instruments in the nose, and does not need to be cut the distal end to obtain the desired length.

It is important to note that the same device can be used to stent the punctum, canaliculus, lacrimal sac, and nasolacrimal duct depending on the post-operative length of the stent.

Figure 21:
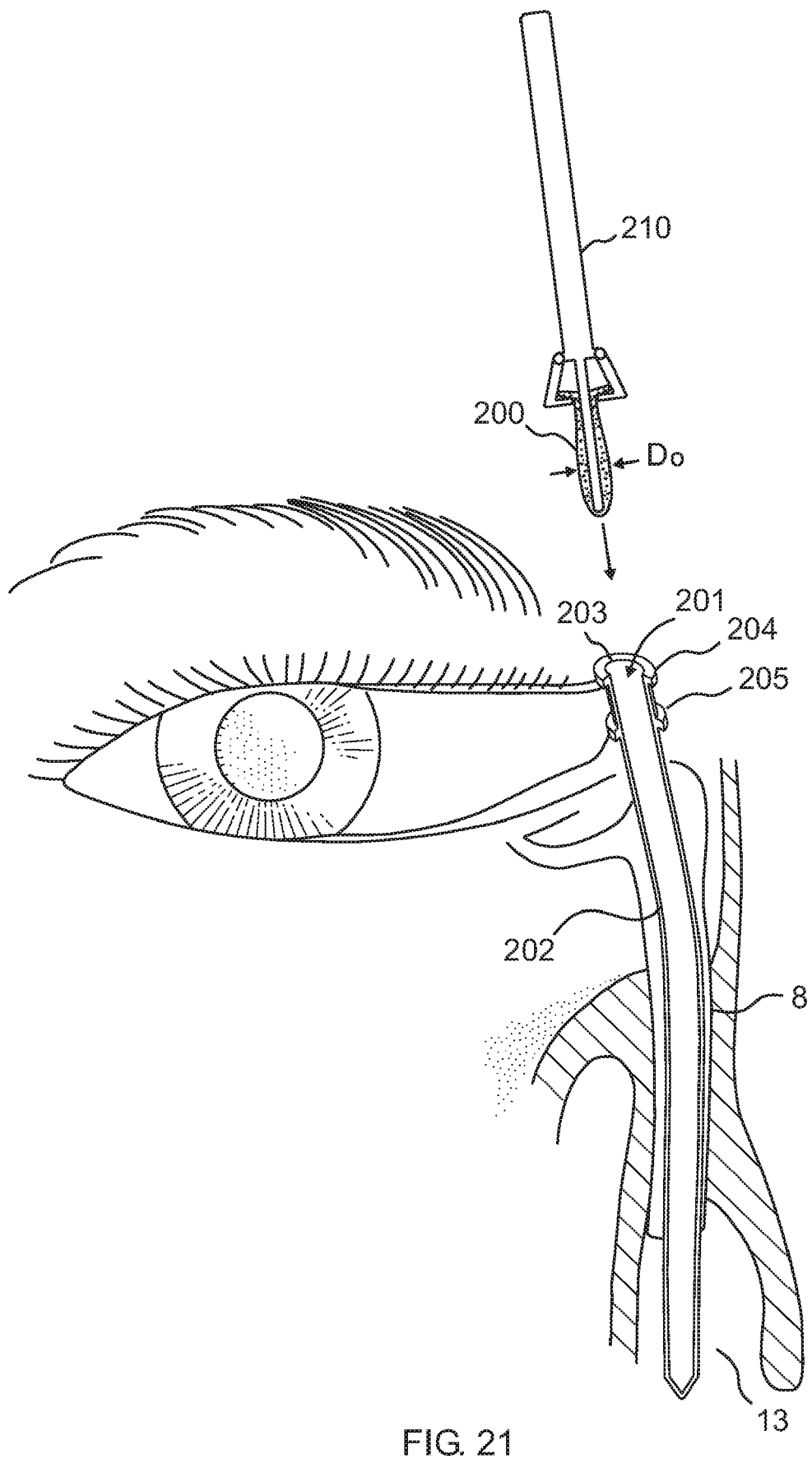
FIG. 21 illustrates an alternate embodiment emplacing the punctal anchor into the expandable central lumen of an emplaced lacrimal stent.

Referring now to FIG. 21, there is shown an alternate punctal anchor 200 which is shaped, dimensioned and made from a material similar to the previous embodiment. In this embodiment the axial bore of the anchor has an open proximal end and a closed distal end. The anchor operates similarly to a punctal plug and is emplaced in a similar manner. However, in this case, rather than a plug contacting a punctum directly, the anchor 200 engages the opening 201 on the proximal extremity 203 of a hollow, flexible stent 202 which has been emplaced according to a previous embodiment and extends from the punctum through the lacrimal duct 8 and into the nasal cavity 13.

The stent 202 has a built-in proximal collar 204 to prevent distal migration into the canaliculus, and a friction enhancing circumferential flange 205 extending from an outer surface portion near the proximal extremity. The flange is positioned either to bear against the walls of the canaliculus or the widened transition between the common canaliculus and the superior and inferior canaliculi and thus discourage proximal migration of the stent.

The anchor 200 is emplaced by first being mounted upon an introducer 210 which operates similarly to an inserter used to insert SNUG PLUGS brand punctum plugs available from FCI Ophthalmics Inc. of Marshfield Hills, Mass. The introducer has a distal prong which engages the bore of the anchor, fingers grasp the collar of the anchor and stretch the anchor axially over the prong. The anchor 200 is selected to have a resiliently reducable diameter so that while it is stretched axially, its outside diameter $D_O$ is reduced. While in the reduced diameter state, the anchor can easily be inserted into the proximal opening 201 of the stent 202.

Figure 22:
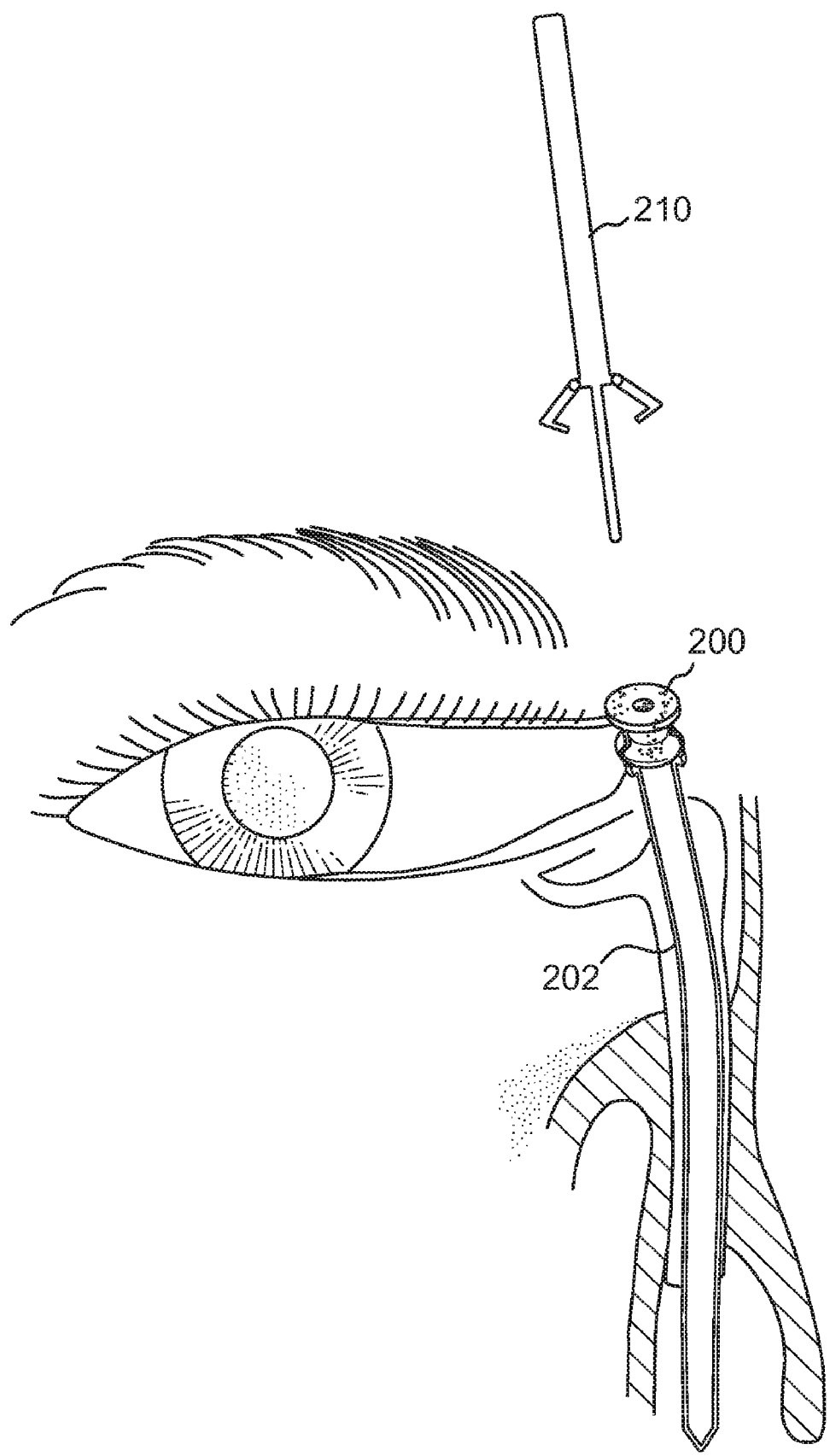
FIG. 22 illustrates the punctal anchor engaging the open proximal end of the stent of FIG. 20.

A shown in FIG. 22, once the anchor 200 is placed into the proximal opening of the stent. The surgeon releases the anchor from the introducer 210. The resiliency of the anchor causes it to return to a diameter expanded state. The resiliency of the stent allows the expanded diameter anchor to widen the diameter of the stent wall forming an over-sized friction fit in the punctal region of the canaliculus.

A further advantage of the instant device is that it can be reversibly emplaced in the lacrimal drainage system. In other words the anchor and the attached stent can be easily removed weeks or months later by grasping it with a forceps and pulling it out of the punctum during a typical office visit.

The punctal anchor introducer/radial expander can also be placed on a silicone tube during a dacryocystorhinostomy ("DCR"). This includes a tube or stent that goes through one or both canaliculi and a prepared opening, directly into the nose. Stenting or intubation of the DCR passageway can be performed similarly to the previously described embodiments. Specifically, after a passageway is formed, the guide sleeve is pushed through the inferomedial wall of the sac, lacrimal fossa, and lateral nasal wall into the nasal cavity. Emplacement is confirmed using the injection of a tracer fluid through the guide sleeve, and suctioning may be conducted through the guide sleeve. The guide sleeve and any rigidizing rod can be withdrawn and the punctal anchor affixed and emplaced.

While the preferred embodiment of the invention has been described, modifications can be made and other embodiments may be devised without departing from the spirit of the invention and the scope of the appended claims.

What is claimed is:

1. A method for stenting a patient's nasolacrimal duct which comprises the steps of:
   selecting an elongated tubular guide sleeve and an elongated flexible stent;
      wherein said guide sleeve has an open proximal end and an open distal end, and defines an internal channel; and,
      wherein said stent has a proximal extremity and a distal extremity; and,
      wherein said stent is located within said channel;
   pushing said sleeve carrying said stent through a patient's punctum, canaliculus, lacrimal sac, nasolacrimal duct and into the nasal cavity;
   confirming that the distal end of said sleeve is located in said nasal cavity;
   proximally withdrawing said guide sleeve while leaving said stent in place; and,
   affixing a punctal anchor to said stent;
   wherein said selecting an elongated flexible stent further comprises:
      choosing said stent to be tubular; and,
      wherein said distal extremity is closed and said proximal extremity is open.

2. A method for stenting a patient's nasolacrimal duct which comprises the steps of:
   selecting an elongated tubular guide sleeve and an elongated flexible stent;
      wherein said guide sleeve has an open proximal end and an open distal end, and defines an internal channel; and,
      wherein said stent has a proximal extremity and a distal extremity; and,
      wherein said stent is located within said channel;
   pushing said sleeve carrying said stent through a patient's punctum, canaliculus, lacrimal sac, nasolacrimal duct and into the nasal cavity;
   confirming that the distal end of said sleeve is located in said nasal cavity;
   proximally withdrawing said guide sleeve while leaving said stent in place; and,
   affixing a punctal anchor to said stent;
   wherein said affixing comprises:
      choosing said stent to have a proximal portion of a given cross-sectional dimension;
      selecting said anchor to have a resiliently expandable bore having a resting diameter smaller than said dimension;
      expanding said bore;
      inserting said proximal portion of said stent into said bore after said expanding; and,
      collapsing said bore onto said stent.

3. A method for stenting a patient's nasolacrimal duct which comprises the steps of:
   selecting an elongated tubular guide sleeve and an elongated flexible stent;
      wherein said guide sleeve has an open proximal end and an open distal end, and defines an internal channel; and,
      wherein said stent has a proximal extremity and a distal extremity; and,
      wherein said stent is located within said channel;
   pushing said sleeve carrying said stent through a patient's punctum, canaliculus, lacrimal sac, nasolacrimal duct and into the nasal cavity;
   confirming that the distal end of said sleeve is located in said nasal cavity;
   proximally withdrawing said guide sleeve while leaving said stent in place; and,
   affixing a punctal anchor to said stent;
   wherein said affixing comprises:
      selecting said anchor to have a resiliently reducable diameter;
      reducing the diameter of said anchor;
      inserting said anchor while in a reduced diameter state into an opening in said proximal extremity of said stent; and,
      allowing said anchor to resiliently return to a non-reduced diameter state, thereby forming a friction fit with said stent.

4. The method of claim 1, wherein said method is practiced in absence of retrieving a portion of said stent out the naris.

5. The method of claim 1, wherein said method is practiced in absence of visualizing said stent within said nasal cavity.

6. The method of claim 1, wherein said confirming comprises:
   injecting a tracing fluid through the guide sleeve; and
   recovering traces of said fluid in said nasal cavity.

7. The method of claim 6, which further comprises:
   inserting a hollow stiffening rod having a distal hole, into the channel of said sleeve; and,
   wherein said injecting comprises:
      attaching a source for said fluid to a proximal connector on said rod.

8. The method of claim 1, wherein said selecting of said guide sleeve comprises:
   choosing said guide to have at least one radial hole near said distal end of said guide sleeve.

9. The method of claim 1, wherein said sleeve has an axial length and wherein said rod has a maximum length dimension greater than two times said axial length.

10. The method of claim 1, which further comprises injecting a lubricant through said channel during said step of pushing.

11. The method of claim 1, which further comprises;
connecting a suction device to the proximal end of said sleeve; and,
suctioning debris out of said system through said channel.

12. The method of claim 1, which further comprises injecting medication into said system through said channel.

13. The method of claim 1, which further comprises:
removing an excess section of said stent located proximally from said anchor after said affixing.

14. The method of claim 13, wherein said removing comprises cutting the stent so that its proximal extremity is flush with the anchor.

15. The method of claim 1, which further comprises:
stiffening said sleeve prior to said pushing.

16. The method of claim 15, wherein said stiffening comprises:
selecting said stent to be tubular defining a central lumen; and,
engaging said lumen with an oblong rod having a first flexural rigidity which is more rigid than a second flexural rigidity of said stent.

17. The method of claim 2, which further comprises:
removing an excess section of said stent located proximally from said anchor after said affixing.

18. The method of claim 17, wherein said removing comprises cutting the stent so that its proximal extremity is flush with the anchor.

19. The method of claim 2, which further comprises:
stiffening said sleeve prior to said pushing.

20. The method of claim 2, wherein said confirming comprises:
injecting a tracing fluid through the guide sleeve; and
recovering traces of said fluid in said nasal cavity.

21. The method of claim 20, which further comprises:
inserting a hollow stiffening rod having a distal hole, into the channel of said sleeve; and,
wherein said injecting comprises:
attaching a source for said fluid to a proximal connector on said rod.

22. The method of claim 2, wherein said selecting of said guide sleeve comprises:
choosing said guide to have at least one radial hole near said distal end of said guide sleeve.

23. The method of claim 2, wherein said sleeve has an axial length and wherein said rod has a maximum length dimension greater than two times said axial length.

24. The method of claim 2, which further comprises injecting a lubricant through said channel during said step of pushing.

25. The method of claim 2, which further comprises;
connecting a suction device to the proximal end of said sleeve; and,
suctioning debris out of said system through said channel.

26. The method of claim 2, which further comprises injecting medication into said system through said channel.

27. The method of claim 3, which further comprises:
removing an excess section of said stent located proximally from said anchor after said affixing.

28. The method of claim 27, wherein said removing comprises cutting the stent so that its proximal extremity is flush with the anchor.

29. The method of claim 3, which further comprises:
stiffening said sleeve prior to said pushing.

30. The method of claim 3, wherein said confirming comprises:
injecting a tracing fluid through the guide sleeve; and
recovering traces of said fluid in said nasal cavity.

31. The method of claim 30, which further comprises:
inserting a hollow stiffening rod having a distal hole, into the channel of said sleeve; and,
wherein said injecting comprises:
attaching a source for said fluid to a proximal connector on said rod.

32. The method of claim 3, wherein said selecting of said guide sleeve comprises:
choosing said guide to have at least one radial hole near said distal end of said guide sleeve.

33. The method of claim 3, wherein said sleeve has an axial length and wherein said rod has a maximum length dimension greater than two times said axial length.

34. The method of claim 3, which further comprises injecting a lubricant through said channel during said step of pushing.

35. The method of claim 3, which further comprises;
connecting a suction device to the proximal end of said sleeve; and,
suctioning debris out of said system through said channel.

36. The method of claim 3, which further comprises injecting medication into said system through said channel.

* * * * *